(12) United States Patent
Medzhitov et al.

(10) Patent No.: US 6,960,343 B2
(45) Date of Patent: Nov. 1, 2005

(54) TOLL/INTERLEUKIN-1 RECEPTOR ADAPTER PROTEIN (TIRAP)

(75) Inventors: Ruslan Medzhitov, New Haven, CT (US); Tiffany Horng, New Haven, CT (US); Gregory Barton, Hamden, CT (US)

(73) Assignee: Yale University School of Medicine, New Haven, CT (US)

( * ) Notice: Subject to any disclaimer, the term of this patent is extended or adjusted under 35 U.S.C. 154(b) by 187 days.

(21) Appl. No.: 10/188,947

(22) Filed: Jul. 3, 2002

(65) Prior Publication Data

US 2003/0023993 A1 Jan. 30, 2003

Related U.S. Application Data

(63) Continuation-in-part of application No. 10/101,398, filed on Mar. 19, 2002, now abandoned.
(60) Provisional application No. 60/289,815, filed on May 9, 2001, provisional application No. 60/289,738, filed on May 9, 2001, and provisional application No. 60/289,866, filed on Aug. 29, 2001.

(51) Int. Cl.[7] .................. A61K 38/17; A61K 38/16; C12P 21/02
(52) U.S. Cl. .................. 424/192.1; 514/12; 530/324; 435/69.7
(58) Field of Search .................. 424/192.1; 514/12; 530/324; 435/69.7

(56) References Cited

U.S. PATENT DOCUMENTS

2002/0164640 A1   11/2002   Sims et al.

FOREIGN PATENT DOCUMENTS

| EP | 1 142 472 A | 10/2001 |
| WO | WO 99/47150 A | 9/1999 |
| WO | WO 00/41561 A | 7/2000 |
| WO | WO 00/60080 | 10/2000 |
| WO | WO 01/88137 | 11/2001 |

OTHER PUBLICATIONS

Result 7 of sequence search in Geneseq database, alignment with Seq ID No: 11 of DE 19526174 A1, printed on Apr. 26, 2005.*
Result 1 of sequence search in US issued patents database, alignment with SEQ ID No: 2 of U.S. Appl. No. 6,399,584, printed on Apr. 26, 2005.*
Hardiman, Gary, et al., "Genetic Structure and Chromosomal Mapping of MyD88," *Genomics*, 45(2):332–339 (Oct. 15, 1997).
Hattori, M., "Homo Sapiens Genomic DNA, Chromosome 11 Clone: RP11–712L6, incomplete sequence," XP002303401, Database EMBL Accession No. AP001318 (Mar. 6, 2000).
Horng, Tiffany, et al., "TIRAP: An Adapter Molecule in the Toll Signaling Pathway," *Nature Immunology*, 2(9): 835–841 (Sep., 2001).
Means, T.K., et al., "Differential Effects of a Toll–Like Receptor Antagonist on *Mycobacterium Tuberculosis*–Induced Macrophage Responses," *Journal of Immunology*, 166(6):4074–4082 (Mar. 15, 2001).

(Continued)

*Primary Examiner*—Robert A. Wax
*Assistant Examiner*—Rosanne Kosson
(74) *Attorney, Agent, or Firm*—Hamilton, Brook, Smith & Reynolds, P.C.

(57) ABSTRACT

TIRAP polypeptides and polynucleotides and methods for producing such polypeptides by recombinant techniques are disclosed. Also disclosed are methods for utilizing TIRAP polypeptides and polynucleotides in therapy, and diagnostic assays for such.

9 Claims, 14 Drawing Sheets

OTHER PUBLICATIONS

Bonnert, T.P., et al., "The cloning and characterization of human MyD88: a member of an IL-1 receptor related family", FEBS Lett., 1997, 402 (1), 81–84.

Fitzgerald, K.A., "Mal (MyD88–adapter–like) is required for Toll–like receptor–4 signal transduction", 2001 Nature 413 (6851), 78–83.

GenBank Accession No. AAB49967.
GenBank Accession No. AAB83958.
GenBank Accession No. AAC50954.
GenBank Accession No. AAC53013.
GenBank Accession No. AAH05584.
GenBank Accession No. AAH05591.
GenBank Accession No. AAH13589.
GenBank Accession No. AAL05037.
GenBank Accession No. AX320365.
GenBank Accession No. CAA35762.
GenBank Accession No. CAD19393.
GenBank Accession No. NP_002459.
GenBank Accession No. NP_034981.
GenBank Accession No. P22366.
GenBank Accession No. P58753.
GenBank Accession No. Q99836.
GenBank Accession No. Q99JY1.
GenBank Accession No. S11226.
GenBank Accession No. XP_087468.

Hardiman, et al., "Molecular characterization and modular analysis of human *MyD88*", 1996, Oncogene 13 (11), pp. 2467–2475.

Horng, T., "TIRAP: an adapter molecule in the Toll signaling pathway", 2001, Nat. Immunol. 2 (9), 835–841.

Lord, et al., "Nucleotide sequence and expression of a cDNA encoding MyD88, a novel myeloid differentiation primary response gene induced by IL6", 1990, Oncogene 5 (7), 1095–1097.

Fitzgerald et al. Mal.(MyD88–adapter–like) is required for Toll–like receptor–4 signal transduction Nature. Sep. 2001, vol. 413, pp. 78–83.

Bonnert et al. The cloning and characterization of human MYD88: a member of an IL–1 receptor related family. FEBS Letters. 1997, vol. 402, pp. 81–84.

Sigmund et al. Viewpoint: Are studies in genetically altered mice out of control? Arterioscler. Thromb. Vasc. Biol. 2000, vol. 20, pp. 1428–1429.

* cited by examiner

No peptide  +TIRAP peptide
0 15' 25' 45'  15' 25' 45'

← IkB-α

FIG. 5D

CpG
No peptide  +TIRAP peptide
0 15' 25' 45'  15' 25' 45'

← PKR-P
← JNK-P
← JNK-P

LPS
No peptide  +TIRAP peptide
0 15' 25' 45'  15' 25' 45'

TOLL/INTERLEUKIN-1 RECEPTOR ADAPTER PROTEIN (TIRAP)

CROSS-REFERENCE TO RELATED APPLICATIONS

This application is a continuation-in-part of U.S. application Ser. No. 10/101,398, filed Mar. 19, 2002, now abandoned which in turn claims priority under 35 U.S.C. §119(e) to U.S. Provisional Application No. 60/289,738, filed May 9, 2001, U.S. Provisional Application No. 60/289,815, also filed May 9, 2001, and U.S. Provisional Application No. 60/289,866, filed Aug. 29, 2001. This application also claims priority to the Patent Cooperation Treaty filing having the Serial No. WO US 02/14915, which was filed on May 9, 2002.

GOVERNMENT FUNDING

This application was funded, at least in part, by a grant from the United States Government, which may have certain rights therein.

BACKGROUND OF THE INVENTION

The drug discovery process is currently undergoing a fundamental revolution as it embraces "functional genomics," that is, high throughput genome- or gene-based biology. This approach is rapidly superceding earlier approaches based on positional cloning. A phenotype, that is a biological function or genetic disease, would be identified and this would then be tracked back to the responsible gene, based on its genetic map position.

Functional genomics relies heavily on the various tools of bioinformatics to identify gene sequences of potential interest from the many molecular biology databases now available. There is a continuing need to identify and characterize further genes and their related polypeptides/proteins, as targets for drug discovery with the potential for affecting immune response.

The strategy of innate immune recognition is based on the detection of constitutive and conserved products of microbial metabolism. Many metabolic pathways and individual gene products are unique to microorganisms and absent from host cells. Although these targets of recognition are not absolutely identical between different species of microbes, the gene products may be found in the context of a common molecular pattern, which is typically highly conserved and invariant among microbes of a given class. Because the targets of innate immune recognition are conserved molecular patterns, they are called pathogen associated molecular patterns (PAMPs).

The recent discovery and characterization of the Toll-like receptor (TLR) family have incited new interest in the field of innate immunity. TLRs are pattern recognition receptors that have a unique and critical function in animal immunity. TLRs typically are transmembrane receptors characterized by an extracellular leucine rich repeats domain and an intracellular TIR (Toll/Interleukin-1 Receptor) domain. The TIR domain is a conserved protein-protein interaction module and plays a role in host defense. In other words, TLRs play a critical role in microbial recognition and control of adaptive immune responses.

In mammalian species, there are at least ten (10) TLRs, and each has a distinct function in innate immune recognition. The TLRs mainly differ from one another with regard to ligand specificity, the use of accessory molecules, expression profiles and differences in signal transduction pathways.

Human TLR4 was the first identified and functionally characterized mammalian Toll. TLR4 functions as the signal transducing receptor for the PAMP lipopolysaccharide (LPS) as well as other PAMPs, which are apparent to one skilled in the art.

Activation of signal transduction pathways by TLRs leads to the induction of a variety of genes that function in host defense including inflammatory cytokines, chemokines, MHC and co-stimulatory molecules. Mammalian TLRs also induce multiple effector molecules such as inducible nitric oxide synthetase and antimicrobial peptides that can directly destroy microbial pathogens.

The signaling pathway, which appears to be shared by all members of the Toll and Interleukin-1 Receptor (IL-1R) families, includes four essential components: the adapters TRAF6, MyD88 and Tollip and a protein kinase, IRAK. MyD88 contains two protein interaction domains: an N-terminal death domain and a C-terminal TIR domain. The TIR domain of MyD88 associates with the TIR domain of TLR and IL-1R, while the death domain interacts with the death domain of IRAK.

In cells wherein MyD88 expression has been suppressed (i.e. in MyD88 knockout mice), macrophages and dendritic cells do not produce cytokines IL-1β, TNF-α, IL-6 and IL-12 when stimulated with LPS, MALP-2 or CpG, which signal through TLR4, TLR2 and TLR9, respectively. Consequently, MyD88 knockout mice are resistant to endotoxic shock. Furthermore, when normal bone marrow-derived dendritic cells (BMDCs) are stimulated with LPS or CpG, they produce large amounts of IL-12 and upregulate cell surface expression of MHC and co-stimulatory molecules. However, in MyD88 deficient BMDCs, stimulation with LPS or CpG does not produce IL-12 or IL-6.

Additionally, RNA-dependent protein kinase (PKR)-deficient cells fail to activate c-Jun N-terminal Kinase (JNK) and p38 MAP Kinase (p38) in response to LPS stimulation. As TLR4 is required for signals downstream of LPS, this indicates that PKR is a component of the TLR4 signaling pathway. Although phosphorylated PKR can be detected in LPS stimulated wild-type macrophages, phosphorylated PKR has also been detected in LPS stimulated MyD88-deficient macrophages. Interestingly, PKR from the MyD88-deficient macrophages was activated with slower kinetics.

Although some cellular responses are completely abolished in MyD88-deficient cells, TLR4, but not TLR9 or TLR2, can still activate NF-κB and MAP kinases. This difference indicates that another adapter protein exists that can mediate MyD88-independent signaling in response to TLR4 ligation.

Thus, there is a need to determine the structure and function of the adapter protein involved in the MyD88 independent signaling downstream of TLR4 for various purposes including to develop compounds to treat diseases related to TLR4 function.

SUMMARY OF THE INVENTION

The present invention relates to Toll Interleukin-1 Receptor Adapter Proteins (TIRAPs), and in particular TIRAP polypeptides and TIRAP polynucleotides, recombinant materials and methods for their production. In yet a further aspect, the present invention relates to TIRAP inhibitors. In another aspect, the invention relates to methods for using such polypeptides and polynucleotides, including the treatment of inflammation and inducing or affecting immune response. In a further aspect, the invention relates to methods for identifying agonists and antagonists/inhibitors using the materials provided by the invention, and treating conditions associated with TIRAP imbalance with the identified compounds. In yet a further aspect, the invention relates to transgenic mammals comprising TIRAP polynucleotides.

BRIEF DESCRIPTION OF THE DRAWINGS

FIG. 1 is a sequence alignment of human and mouse TIRAP.

FIG. 2, comprising

FIG. 3, comprising

FIG. 4, comprising

FIG. 5, comprising FIGS. 5A through 5D, is a series of blots depicting inhibition of LPS- but not CpG-induced NF-κB activation, PKR phosphorylation, and JNK phosphorylation by TIRAP. (A) TIRAP peptide, but not a reverse sequence peptide, inhibited LPS-induced NF-κB activation. RAW κB cells pretreated for 1 h with either the TIRAP or control peptide were stimulated with LPS (10 ng/ml) for 5 h. Samples were stimulated in duplicate. (B) Pretreatment of RAW cells with TIRAP peptide blocks LPS-induced IκB-α degradation. RAW cells pretreated with the TIRAP peptide as indicated were either left unstimulated or stimulated with LPS (10 ng/ml) for the indicated time periods. Lysates (30 μg/sample) were resolved by SDS-PAGE followed by immunoblotting with an anti-IκB-α antibody to assess IκB-α degradation. (C) TIRAP peptide inhibited LPS- but not CpG-induced NF-κB activity. RAW κB cells pretreated with the TIRAP peptide as indicated were stimulated with either LPS or CpG and harvested for reporter assay. (D) TIRAP peptide inhibited PKR and JNK phosphorylation induced by LPS but not CpG. RAW cells either untreated or pretreated with 40 μM of the TIRAP peptide were stimulated with either LPS or CpG as indicated. Lysates (30 μg/sample) were analyzed by SDS-PAGE followed by immunoblotting with antibodies that specifically recognize phosphorylated PKR or phosphorylated JNK.

FIG. 6, comprising

DESCRIPTION OF THE INVENTION

Figure 2A:
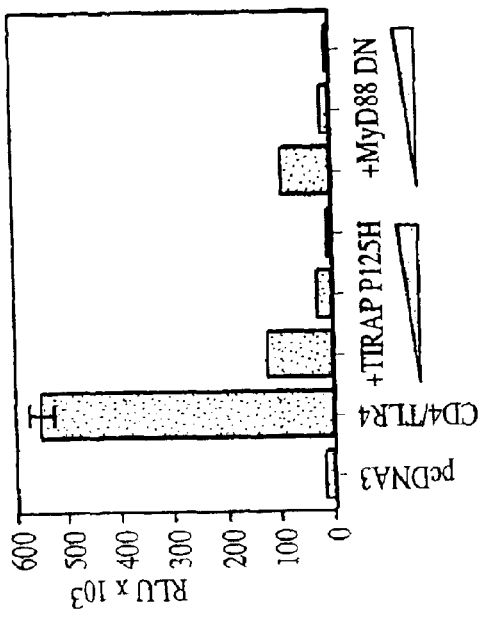
FIGS. 2A through 2D, is a series of graphs which demonstrate that TIRAP is a component of the TLR4 signaling pathway, but not of the IL-1R signaling pathway. On the y axis, luciferase activity is expressed as fold induction or relative light units (RLU). The x axis shows the transfected constructs: pcDNA3 (control vector); TIRAP (encodes full length TIRAP); TIRAP N (encodes N-terminal domain of TIRAP); TIRAP C (encodes C-terminal domain of TIRAP); TIRAP P125H (encodes TIRAP containing mutation at amino acid 125); CD4/TLR4 (encodes constitutively active form of CD4); MyD88 DN (encodes dominant negative mutant of MyD88); IL-1R/AcP (encodes ILI-1 receptor and receptor accessory protein); TLR9 (encodes full length TLR9). Shaded triangles below the constructs indicate that increasing amounts of that construct was added.

As described briefly above, some cellular responses are completely abolished in MyD88-deficient cells, yet TLR4, but not TLR9 or TLR2, can still activate NF-κB and MAP kinases. Specifically, a detailed analysis of the NF-κB and MAP signaling pathways demonstrates that the pathogen associated molecular pattern (PAMP) LPS, but not CpG or MALP-2, induces activation of NF-κB, JNK, p38 and ERK in MyD88 deficient cells. Activation of these signaling pathways occurred with delayed kinetics and was insufficient for the induction of cytokine gene expression.

Furthermore, MyD88 deficient BMDCs stimulated with LPS or CpG do not produce IL-12 or IL-6. However, BMDCs can be induced to upregulate expression of MHC and co-stimulatory molecules (such as CD80 and CD86), when treated with LPS, but not when stimulated with CpG. This result demonstrates that a MyD88 independent signaling pathway is sufficient for dendritic cell maturation, whereas the MyD88-dependent signaling pathway is required for the induction of cytokines IL-6 and IL-12. In addition, caspase-1 processing of Interleukin-18 into its biologically active form can be induced by TLR4, independently of MyD88.

These differences indicate that another adapter protein exists that can mediate MyD88-independent signaling in response to TLR4 ligation. As used herein, the adapter protein that mediates MyD88 independent signaling in response to TLR4 ligation will be referred to as "TIRAP" (Toll/Interleukin-1 Receptor Adapter Protein).

In particular, polypeptides of the present invention include isolated polypeptides encoded by the human and mouse polynucleotides comprising the sequences set forth in SEQ ID NO:1 and 2, respectively. Polypeptides of the present invention are believed to be members of the Toll/Interleukin-1 Receptor Adapter Protein family including MyD88. This gene is therefore of interest because it presents an alternative mechanism to induce or inhibit dendritic cell maturation as well as activation of NF-κB, JNK, p38 and ERK in cells.

As one of skill in the art understands, TLR4 is involved in numerous physiological responses, including infection and cell damage. For example, as indicated above TLR4 recognizes the PAMP, LPS. TLR4 has also been implicated in inflammation responses, and in particular cellular necrosis induced inflammation. Accordingly, the discovery and characterization of molecules that affect and/or are involved in the signal pathways of TLR4 is important for the development of effective treatments for the above-described conditions as well as other conditions which will be appreciated by one of skill in the art.

TIRAP and TIRAP Inhibitor Polynucleotides and Polypeptides Generally

Figure 1:
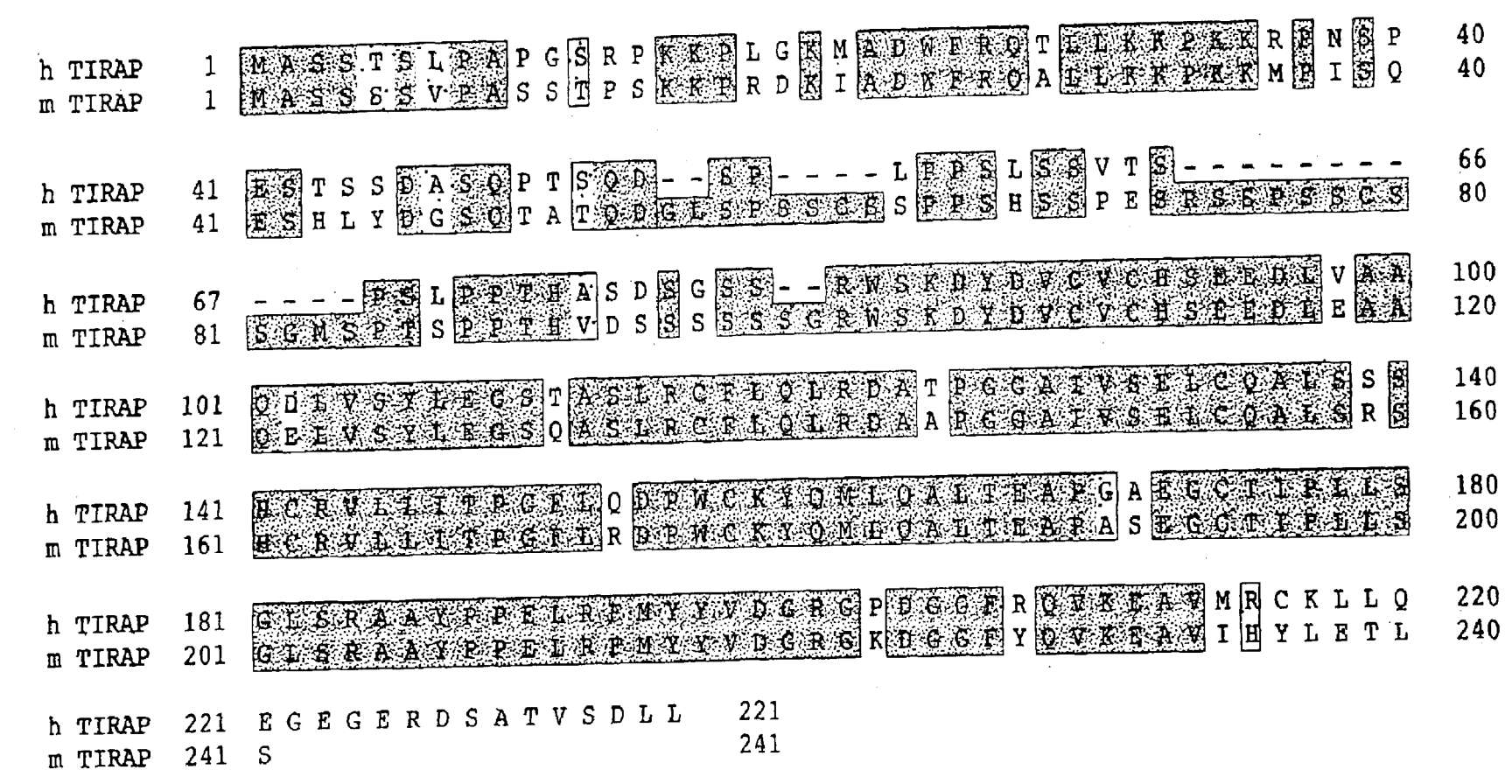

In a first aspect, the present invention relates to TIRAP polynucleotides and TIRAP polypeptides. Specifically, the polynucleotides set forth in SEQ ID NO: 1 and 2 encode the polypeptides set forth in SEQ ID NOS:3 (human) and 4 (mouse), respectively, which comprise Toll Interleukin-1 Receptor Adapter Proteins. The human and mouse polynucleotides encoding TIRAP are highly homologous (See FIG. 1). Specifically, in one embodiment, a comparison of human and mouse TIRAP polynucleotides and polypeptides indicates at least 73% identity at the protein level and 83% identity at the polynucleotide level. Thus it will be understood, based on the present disclosure, that both human and mouse TIRAP polynucleotides and the polypeptides encoded thereby can be used for similar purposes, as described herein. The polynucleotides and polypeptides set forth in SEQ ID NOS:1–4 are the full length TIRAP molecules and are hereinafter referred to generally as TIRAP or TIRAP polynucleotides, TIRAP peptides and TIRAP polypeptides. Unless otherwise specified, "TIRAP" is synonymous with "TIRAP polypeptide," and is meant to refer to the Toll Interleukin-1 Receptor Adapter Protein and other polypeptides that have the same biological function, i.e., that modulate MyD88 independent signaling in response to activation of TLRs by PAMPs. The properties of the polypeptides set forth in SEQ ID NOS:3 and 4 are also hereinafter referred to as "TIRAP activity" or "TIRAP polypeptide activity" or "biological activity of TIRAP," as explained below.

Preferred polypeptides and polynucleotides of the present invention having homology to TIRAP polynucleotides and polypeptides as explained below, are expected to have similar biological functions/properties to TIRAP polypeptides and polynucleotides. Specifically, preferred TIRAP polypeptides of the present invention have TIRAP activity in that they can bind to the TIRAP binding domain of TLR4. Such TIRAP polypeptides are therefore useful for drug screening, e.g., as described below. the TIRAP polypeptides of the invention also include such polypeptides that, upon activation of TLR4, signal a MyD88 independent response, e.g., activation of NF-κB and MAP kinases.

The characterization of the TIRAP polypeptide and the polynucleotide encoding the TIRAP polypeptide has led to the discovery of compounds that inhibit both the MyD88 independent pathway as well as the MyD88 dependent pathway of TLR4 by inhibiting TIRAP polypeptide mediated signaling. Such compounds that inhibit TIRAP activity are useful to prevent or reduce inflammation and septic shock, and in particular to assist in the prevention of graft rejection, which occurs, at least in part, because of cellular necrosis induced inflammation.

Therefore, in a second aspect, the present invention relates to TIRAP inhibitors. Specifically, the polypeptides set forth in SEQ ID NOS:9 and 10 are human and mouse, respectively, TIRAP inhibitor polypeptides. These polypeptides are referred to herein as TIRAP inhibitors or TIRAP mutant peptides or TIRAP inhibitor polypeptides. The properties of each of the TIRAP inhibitors are hereinafter referred to as "TIRAP inhibitor activity." The polynucleotides set forth in sequences SEQ ID NO:5 (naturally occurring) and SEQ ID NO:6 (degenerate) encode the human TIRAP inhibitor polypeptide set forth in SEQ ID NO:9, and the polynucleotide set forth in sequences SEQ ID NO:7 (naturally occurring) and SEQ ID NO:8 (degenerate) encode the mouse TIRAP inhibitor polypeptide set forth in SEQ ID NO:10. The SEQ ID NOS:5–8 are referred to as TIRAP inhibitor polynucleotides and the sequences set forth in SEQ ID NOS:9 and 10 are referred to as TIRAP inhibitor polypeptides. SEQ ID NO:12, which corresponds to an interactive region of MyD88, is also a TIRAP inhibitor.

Preferred inhibitor polypeptides and inhibitor polynucleotides of the present invention, having homology to TIRAP inhibitor polypeptides and polynucleotides as explained further below, are expected to have similar biological functions/properties to TIRAP inhibitor polypeptides and polynucleotides. As used herein, preferred TIRAP inhibitor polypeptides of the present invention have TIRAP inhibitor activity in that they can, notwithstanding activation of TLR4, inhibit both the MyD88 independent response, e.g., activation of NF-κB and MAP kinases and the MyD88 dependent response in cells expressing TLR4, as described in more detail below.

Lastly, SEQ ID NO:11 is a functional example of a fusion protein of the instant invention, and particularly a fusion protein of Antennapedia and a TIRAP inhibitor polypeptide. Specifically, SEQ ID NO:11 is a fusion protein of Antennapedia and the TIRAP inhibitor set forth in SEQ ID NO: 10. Because the polypeptide set forth in SEQ ID NO:11 also inhibits TIRAP activity, the properties of the TIRAP inhibitor fusion protein are also referred to as "TIRAP inhibitor activity." This particular embodiment is described in more detail below under the heading "Fusion Proteins."

The Structure of Polypeptides and Polynucleotides of the Present Invention

The polypeptides of the present invention may be in the form of the "mature" protein or may be a part of a fusion protein, e.g., SEQ ID NO:11, as described below under "Fusion Proteins." Such fusion proteins of the invention include additional amino acid sequences which are useful in expression, purification or formulation, e.g., secretory or leader sequences, pro-sequences, sequences which aid in purification such as multiple histidine residues or ligand binding sites, cleavage sites, or other sequences for stability during recombinant production. Fusion proteins, as encompassed by the present invention, do not encompass fragments of naturally occurring polypeptides fused to the remaining naturally occurring sequences of that polypeptide.

The present invention also includes polypeptides that differ from a reference polypeptide by one or more conservative amino acid substitutions, whereby a residue is removed and substituted with another residue with like characteristics. Typical such substitutions can be among Ala, Val, Leu and Ile; among Ser and Thr; among the acidic residues Asp and Glu; among Asn and Gln; and among the basic residues Lys and Arg; or aromatic residues Phe and Tyr. Polypeptides having at least one conservative amino acid substitution are referred to herein as "variants."

Polypeptides of the invention therefore also include polypeptides which are fusion proteins of the polypeptides or which contain conservative amino acid substitutions, as described above, and which, excluding fused sequences, have at least 92% identity, most preferably 100% identity, to the sequences of SEQ ID NOS:4, 9, 10, 11 and 12 over the entire length of SEQ ID NOS:4, 9, 10, 11 and 12, either before or after any conservative amino acid substitutions. Such polypeptides include a polypeptide comprising the polypeptide set forth in SEQ ID NOS:4, 9, 10, 11 and 12, as well as a polypeptide consisting of the polypeptide set forth in SEQ ID NOS:4, 9, 10, 11 and 12.

Polypeptides of the present invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

Polynucleotides of the present invention include isolated polynucleotides that encode a polypeptide of the invention as well as such polynucleotides that are incorporated into a recombinant DNA molecule including, e.g., a DNA molecule further including sequences useful for cloning or expressing the polypeptides of the invention, many of which are apparent to one of skill in the art. Such recombinant DNA molecules can include, e.g., promoter regions, selection markers, sequences required for integration or replication, etc. In addition, polynucleotides of the present invention include sequences having conservative codon substitutions, i.e., substitutions that do not affect the amino acid sequence of the encoded polypeptide of the invention. Such substitutions are well known in the art. Polynucleotide sequences of the invention therefore include recombinant DNA molecules having the sequences of the invention as well as sequences that have conservative codon substitutions, for example substituting the codon ACC with ACA, both of which code for threonine.

Accordingly, polynucleotides of the invention also include polynucleotides which have at least 92% identity, preferably at least 95% identity, most preferably 100% identity, to the sequences of SEQ ID NOS: 2, 5, 6, 7, and 8 over the entire length of SEQ ID NOS: 2, 5, 6, 7, and 8.

Such polynucleotides include a polynucleotide comprising the polynucleotide set forth in SEQ ID NO:2 as well as the polynucleotide consisting of the polynucleotide set forth in SEQ ID NO:2. Such polynucleotides also include polynucleotides comprising the polynucleotides set forth in SEQ ID NO:5–8 as well as the polynucleotides consisting of the polynucleotides set forth in SEQ ID NO:5–8.

The invention also provides polynucleotides that are complementary to all the above-described polynucleotides.

TIRAP Inhibitors

As set forth above, the polypeptides of the invention which include among others SEQ ID NOS:9–12, are TIRAP inhibitor polypeptides. The polypeptides set forth in SEQ ID NOS:9 and 10 are mutated forms of the binding domain of the polypeptides set forth in SEQ ID NO:3 and 4, respectively, the TIRAP polypeptide.

Preferably, an effective TIRAP inhibitor polypeptide of the present invention has an encoded histidine to proline mutation at amino acid position 145 (as measured in mouse TIRAP, shown in FIG. 1), or the proline to histidine mutation at amino acid position 125 (as measured in human TIRAP, also shown in FIG. 1 and referenced in the Figures as P125H) relative to the TIRAP polypeptide which does not have the encoded mutation. The mutation may be accomplished using techniques well understood to those of skill in the art.

It has been found that the histidine to proline mutation at the appropriate position enables a TIRAP inhibitor to bind to the cytoplasmic domain of TLR4, yet inhibit downstream signaling of TLR4 (both MyD88 dependent and MyD88 independent signaling).

Without ascribing to a particular theory of cellular receptor signaling, it is believed that TIRAP inhibitors, as well as other polypeptides that are sufficiently homologous to TIRAP inhibitors or TIRAP inhibitor mimetics which have TIRAP inhibitor activity, bind to TLR4. This binding is conceptually illustrated in FIG. 7. Once bound, the TIRAP inhibitor can inhibit TLR4 signaling through the MyD88 dependent pathway as well as the MyD88 independent pathway.

As suggested in the preceding paragraph, an organic compound, typically with a molecular weight under 2 KD, having appropriate structural similarity to a TIRAP inhibitor polypeptide may be also used as a TIRAP inhibitor. For example, a small molecule mimetic may be used. As one of skill in the art understands, small molecule mimetics are chemically synthesized compounds that provide the spatial conformation necessary to properly associate to a particular protein and elicit a response. Therefore, the present invention also comprises the use of a small molecule mimetic to inhibit TIRAP signaling.

Fusion Proteins

A further aspect of the invention also relates to polynucleotides encoding fusion proteins. Examples of fusion protein technology can be found in International Patent Application Nos. WO 94/29458 and WO 94/22914, the contents of which are hereby incorporated by reference.

This particular embodiment of the present invention relates to fusion proteins comprising a TIRAP inhibitor polypeptide, or an active portion or active fragment thereof, and a cellular membrane transport protein, such as Antennapedia. As one of skill in the art understands, delivering proteins across the cell membrane so they become therapeutically active can be difficult. Viruses or virus fragments can be used to transport proteins into cells, but this technology is not universally approved. Antennapedia, obtained from the fruit fly Drosophila, is virtually identical to the human form of the protein and thus, there is little, if any, antigenic response in human use. Even though proteins can be transported using a part of Antennapedia (e.g., Antp16), such a method is typically only suitable for small proteins.

Although many embodiments of fusion proteins having TIRAP inhibitor activity are envisioned, one functional example of such an embodiment is set forth in SEQ ID NO:11, which represents a fusion of Antennapedia and the TIRAP inhibitor set forth in SEQ ID NO:10. It has been found that the TIRAP inhibitors set forth in SEQ ID NOS:9 and 10 are of the appropriate size to be conjugated to Antennapedia and transported across cellular membranes. Specifically, once conjugated to a TIRAP inhibitor Antennapedia facilitates transport of the TIRAP inhibitor across the cellular membrane so that the polypeptide become therapeutically active within the cell and exhibits TIRAP inhibitor activity.

Methods of Treating Abnormal Conditions

In a further aspect, the present invention provides methods of treating abnormal conditions such as, for instance, inflammation, related to either an excess of, or an under-expression of, TIRAP polypeptide activity. Preferably, the practice of this invention would comprise antagonizing or agonizing TIRAP activity to prevent or treat an inflammatory response.

If the activity of the TIRAP polypeptide is in excess, several approaches are available. One approach comprises administering to a subject in need thereof a TIRAP inhibitor polypeptide or TIRAP inhibitor mimetic (antagonist) as hereinabove described, optionally in combination with a pharmaceutically acceptable carrier, in an amount effective to inhibit the function of the polypeptide, such as, for example, by 1) binding an inhibitory molecule to TIRAP itself, thereby inhibiting TIRAP function, or 2) by blocking the binding of TIRAP to TLR4 by binding a TIRAP inhibitor to TLR4 and thereby potentially inhibit both MyD88 dependent and independent signaling.

In still another approach, expression of the gene encoding an endogenous TIRAP polypeptide can be inhibited using expression-blocking techniques. Known techniques involve the use of antisense sequences, either internally generated or separately administered (see, for example, O'Connor, J Neurochem (1991) 56:560 in Oligodeoxynucleotides as Antisense Inhibitors of Gene Expression, CRC Press, Boca Raton, Fla. (1988)). Alternatively, oligonucleotides which form triple helices with the gene can be supplied (see, for example, Lee et al., Nucleic Acids Res (1979) 6:3073; Cooney et al., Science (1988)241:456; Dervan et al., Science (1991)251:1360). These oligomers can be administered per se or the relevant oligomers can be expressed in vivo.

For treating abnormal conditions related to an under-expression of TIRAP and its activity, several approaches are also available. One approach comprises administering to a subject a therapeutically effective amount of a compound which activates a polypeptide of the present invention, i.e., an agonist in combination with a pharmaceutically acceptable carrier (described below in the next section), to thereby alleviate the abnormal condition. Alternatively, gene therapy may be employed to effect the endogenous production of TIRAP by the relevant cells in the subject. For example, a polynucleotide of the invention may be engineered for expression in a replication defective retroviral vector, as discussed above. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a subject for engineering cells in vivo and expression of the polypeptide in vivo. For an overview of gene therapy, see Chapter 20, Gene Therapy and other Molecular Genetic-based Therapeutic Approaches, (and references cited therein) in Human Molecular Genetics, T Strachan and A P Read, BIOS Scientific Publishers Ltd (1996). Another approach is to administer a therapeutic amount of a polypeptide of the present invention in combination with a suitable pharmaceutical carrier.

Pharmaceutical Applications

In a further aspect, the present invention provides for pharmaceutical compositions comprising a therapeutically effective amount of a polypeptide, such as the soluble form of a polypeptide of the present invention, agonist/antagonist peptide or small molecule compound, in combination with a pharmaceutically acceptable carrier or excipient. Such carriers include, but are not limited to, saline, buffered saline, dextrose, water, glycerol, ethanol, and combinations thereof. The invention further relates to pharmaceutical packs and kits comprising one or more containers filled with one or more of the ingredients of the aforementioned compositions of the invention. Polypeptides and other compounds of the present invention may be employed alone or in conjunction with other compounds, such as therapeutic compounds.

The composition will be adapted to the route of administration, for instance by a systemic or an oral route. Preferred forms of systemic administration include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if a polypeptide or other compounds of the present invention can be formulated in an enteric or an encapsulated formulation, oral administration may also be possible. Administration of these compounds may also be topical and/or localized, in the form of salves, pastes, gels, and the like.

The dosage range required depends on the choice of peptide or other compounds (such as a small molecule mimetic) of the present invention, the route of administration, the nature of the formulation, the nature of the subject's condition, and the judgment of the attending practitioner. Suitable dosages, however, are typically in the range of 0.1–100 µg/kg of subject. Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Polypeptides used in treatment can also be generated endogenously in the subject, in treatment modalities often referred to as "gene therapy" as described above. Thus, for example, cells from a subject may be engineered with a polynucleotide, such as a DNA or RNA, to encode a polypeptide ex vivo, and for example, by the use of a retroviral plasmid vector. The cells are then introduced into the subject.

Polynucleotide and polypeptide sequences form a valuable information resource with which to identify further sequences of similar homology. Storing the sequence in a computer readable medium and then using the stored data to search a sequence database using well known searching tools, such as GCC most easily facilitates this. Accordingly, in a further aspect, the present invention provides for a computer readable medium having stored thereon a polynucleotide comprising the sequence of SEQ ID NOS:1, 2 and 5–8.

Methods of Production of Polypeptides and Polynucleotides

Polynucleotides of the present invention may be obtained, using standard cloning and screening techniques. Polynucleotides of the invention can also be obtained from natural sources such as genomic DNA libraries or can be synthesized using well known and commercially available techniques. Polypeptides of the invention can also be synthesized using well known and commercially available techniques.

When polynucleotides of the present invention are used for the recombinant production of polypeptides of the present invention, the polynucleotide may include the coding sequence for the mature polypeptide, by itself, or the coding sequence for the mature polypeptide in reading frame with other coding sequences, such as those encoding a leader or secretory sequence, a pre-, or pro- or prepro- protein sequence, or other fusion peptide portions. For example, a marker sequence, which facilitates purification of the fused polypeptide, can be encoded. In certain preferred embodiments of this aspect of the invention, the marker sequence is a hexa-histidine peptide, as provided in the pQE vector (Qiagen, Inc.) and described in Gentz et al., Proc Natl Acad Sci USA (1989) 86:821–824, or is an HA tag. The polynucleotide may also contain non-coding 5' and 3' sequences, such as transcribed, non-translated sequences, splicing and polyadenylation signals, ribosome binding sites and sequences that stabilize mRNA.

Polynucleotides which are identical or sufficiently identical to a nucleotide sequence contained in SEQ ID NOS:1, 2 and 5–8 may be used as hybridization probes for cDNA and genomic DNA or as primers for a nucleic acid amplification (PCR) reaction, to isolate full-length cDNAs and genomic clones encoding polypeptides of the present invention and to isolate cDNA and genomic clones of other genes (including genes encoding homologs and orthologs from species other than human) that have a high sequence similarity to SEQ ID NOS:1, 2 and 5–8. The probes or primers will generally comprise at least 15 nucleotides, preferably, at least 30 nucleotides and may have at least 50 nucleotides. Particularly preferred probes will have between 30 and 50 nucleotides.

A polynucleotide encoding a polypeptide of the present invention, including homologs and orthologs from species other than human, may be obtained by a process which comprises the steps of screening an appropriate library (as understood by one of ordinary skill in the art) under stringent hybridization conditions with a labeled probe having the sequence of SEQ ID NO:1, 2 or 5–8 or a fragment thereof; and isolating full-length cDNA and genomic clones containing said polynucleotide sequence. Such hybridization techniques are well known to the skilled artisan. Preferred stringent hybridization conditions include overnight incubation at 42 degrees Celsius in a solution comprising: 50% formamide, 5×SSC (150 mM NaCl, 15 mM trisodium citrate), 50 mM sodium phosphate (pH 7.6), 5× Denhardt's solution, 10% dextran sulfate, and 20 microgram/ml denatured, sheared salmon sperm DNA; followed by washing the filters in 0.1×SSC at about 65 degree C. Thus the present invention also includes polynucleotides obtainable by screening an appropriate library under stringent hybridization conditions with a labeled probe having the sequence of SEQ ID NO:1, 2 or 5–8.

The skilled artisan will appreciate that, in many cases, an isolated cDNA sequence will be incomplete, in that the region coding for the polypeptide is cut short at the 5' end of the cDNA. This is a consequence of reverse transcriptase, an enzyme with inherently low processivity (a measure of the ability of the enzyme to remain attached to the template during the polymerization reaction), failing to complete a DNA copy of the mRNA template during 1st strand cDNA synthesis.

There are several methods available and well known to those skilled in the art to obtain full-length cDNAs, or extend short cDNAs, for example those based on the method of Rapid Amplification of cDNA ends (RACE) (see, for example, Frohman et al., PNAS USA 85, 8998–9002, 1988). Recent modifications of the technique, exemplified by the Marathon® technology (Clontech Laboratories Inc.) for example, have significantly simplified the search for longer cDNAs. In the Marathon® technology, cDNAs have been prepared from mRNA extracted from a chosen tissue and an 'adapter' sequence ligated onto each end. Nucleic acid amplification (PCR) is then carried out to amplify the 'missing' 5' end of the cDNA using a combination of gene specific and adapter specific oligonucleotide primers. The PCR reaction is then repeated using 'nested' primers, that is, primers designed to anneal within the amplified product (typically an adapter specific primer that anneals further 3' in the adapter sequence and a gene specific primer that anneals further 5' in the known gene sequence). The products of this reaction can then be analyzed by DNA sequencing and a full-length cDNA constructed either by joining the product directly to the existing cDNA to give a complete sequence, or carrying out a separate full-length PCR using the new sequence information for the design of the 5' primer.

Recombinant polypeptides of the present invention may be prepared by processes well known in the art from genetically engineered host cells comprising expression systems. Accordingly, in a further aspect, the present invention relates to expression systems which comprise a polynucleotide or polynucleotides of the present invention, to host cells which are genetically engineered with such expression systems and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al., Basic Methods in Molecular Biology (1986) and Sambrook et al., Molecular Cloning: A Laboratory Manual, 2nd Ed., Cold Spring Harbor Laboratory Press, Cold Spring Harbor, N.Y. (1989). Preferred such methods include, for instance, calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as *streptococci, staphylococci, E. coli, Streptomyces* and *Bacillus subtilis* cells; fungal cells, such as yeast cells and *Aspergillus* cells; insect cells such as *Drosophila* S2 and *Spodoptera* Sf9 cells; animal cells such as CHO, COS, HeLa, C127, 3T3, BHK, HEK 293 and Bowes melanoma cells; and plant cells.

A great variety of expression systems can be used, for instance, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector which is able to maintain, propagate or express a polynucleotide to produce a polypeptide in a host may be used. The appropriate nucleotide sequence may be inserted into an expression system by any of a variety of well-known and routine techniques, such as, for example, those set forth in Sambrook et al., MOLECULAR CLONING, A LABORATORY MANUAL (supra). Appropriate secretion signals may be incorporated into the desired polypeptide to allow secretion of the translated protein into the lumen of the endoplasmic reticulum, the periplasmic space or the extracellular environment. These signals may be endogenous to the polypeptide or they may be heterologous signals.

If a polypeptide of the present invention is to be expressed for use in screening assays (described below), the peptide may be produced intracellularly or secreted into the medium. If produced intracellularly, the cells must first be lysed before the polypeptide is recovered. The peptide may be membrane bound, for example, it may be fused with the cytoplasmic domain of a membrane protein, or it may contain sequence motifs which will undergo a lipid modification, such as palmitolyation, that will target the peptide to the plasma membrane. If the polypeptide is secreted into the medium, the medium can be recovered in order to recover and purify the polypeptide.

Polypeptides of the present invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, and lectin chromatography. Most preferably, high performance liquid chromatography is employed for purification. Well-known techniques for refolding proteins may be employed to regenerate active conformation when the polypeptide is denatured during isolation and or purification.

Screening Techniques for TIRAP and TIRAP Inhibitors

As described above, TIRAP plays a role in many biological functions, including many disease states, in particular inflammation, septic shock and necrosis induced inflammation. It is therefore desirous to devise screening methods to identify compounds which stimulate or which inhibit the function of the TIRAP polypeptide. Accordingly, in a further aspect, the present invention provides for a method of screening compounds to identify those which stimulate or which inhibit the function of TIRAP. In general, agonists or antagonists may be employed for therapeutic and prophylactic purposes (described above). Appropriate compounds may be identified from a variety of sources, for example, cells, cell-free preparations, chemical libraries, and natural product mixtures.

The screening method may simply measure the binding of a candidate compound to a polypeptide of the present invention, or a small molecule mimetic, or to cells or membranes bearing a polypeptide of the present invention, or a fusion protein thereof by means of a label directly or indirectly associated with the candidate compound. Alternatively, the screening method may involve competition with a labeled competitor. Further, these screening methods may test whether the candidate compound results in a signal generated by activation or inhibition of the polypeptide, using detection systems appropriate to the cells bearing the polypeptide.

Inhibitors of activation are generally assayed in the presence of a known agonist and the effect on activation by the agonist by the presence of the candidate compound is observed. Constitutively active polypeptides may be employed in screening methods for inverse agonists or inhibitors, in the absence of an agonist or inhibitor, by testing whether the candidate compound results in inhibition of activation of the polypeptide. Further, the screening methods may simply comprise the steps of mixing a candidate compound with a solution containing a polypeptide of the present invention, to form a mixture, measuring TIRP activity in the mixture, and comparing TIRAP activity of the mixture to a standard. In other words, the screening method comprises the steps of providing a polypeptide comprising at least the TIRAP-binding domain of TLR4, a TIRAP polypeptide or other polypeptide that comprises a TLR4 binding domain, and a candidate compound, placing the candidate compound into proximity with the polypeptide comprising the TIRAP-binding domain of TLR4 and the TIRAP polypeptide or other polypeptide, and determining whether the candidate compound competes with the binding of either of the polypeptide comprising the TIRAP-binding domain of TLR4 or the TIRAP polypeptide or other polypeptide.

As one skilled in the art understands, fusion proteins, such as those made from a Fc portion of a polypeptide and a TIRAP polypeptide can also be used for high-throughput screening assays to identify antagonists for the polypeptide of the present invention (see D. Bennett et al., J Mol Recognition, 8:52–58 (1995); and K. Johanson et al., J. Biol Chem, 270:9459–9471 (1995)).

Examples of potential polypeptide antagonists include antibodies or, in some cases, oligonucleotides or proteins which are closely related to the ligands, substrates, receptors, enzymes, etc., as the case may be, of the polypeptide, e.g., a fragment of the ligands, substrates, receptors, enzymes, etc.; or small molecules which bind to the polypeptide of the present invention but do not elicit a response, so that the activity of the polypeptide is prevented.

The polynucleotides, polypeptides and antibodies of the present invention may also be used to configure screening methods for detecting the effect of added compounds on the production of mRNA and polypeptide in cells. For example, an ELISA assay may be constructed for measuring secreted or cell associated levels of polypeptide using monoclonal and polyclonal antibodies by standard methods known in the art. This can be used to discover agents which may inhibit or enhance the production of polypeptide from suitably manipulated cells or tissues.

Thus, in another aspect, the present invention relates to a screening kit for identifying agonists, antagonists, other ligands and receptors, substrates, enzymes, etc. for polypeptides of the present invention; or compounds which decrease or enhance the production of such polypeptides, which comprises:

(a) a polypeptide of the present invention;
(b) a recombinant cell expressing a polypeptide of the present invention;
(c) a cell membrane expressing a polypeptide of the present invention; or
(d) antibody to a polypeptide of the present invention;
which polypeptide is preferably that of SEQ ID NOS:3 or 4. It will be appreciated that in any such kit, (a), (b), (c) or (d) may comprise a substantial component.

It will be readily appreciated by the skilled artisan that a polypeptide of the present invention may also be used in a method for the structure-based design of an agonist, antagonist or inhibitor of the polypeptide, by:

(a) determining in the first instance the three-dimensional structure of the polypeptide;

(b) deducing the three-dimensional structure for the likely reactive or binding site(s) of an agonist, antagonist or inhibitor;

(c) synthesizing candidate compounds that are predicted to bind to or react with the deduced binding or reactive site; and (d) testing whether the candidate compounds are indeed agonists, antagonists or inhibitors.

It will be further appreciated that this will normally be an iterative process.

Antigenic Properties of the Polynucleotides and Polypeptides of the Present Invention The polypeptides of the invention or their fragments or analogs thereof, or cells expressing them, can also be used as immunogens to produce antibodies immunospecific for polypeptides of the present invention. The term "immunospecific" means that the antibodies have substantially greater affinity for the polypeptides of the invention than their affinity for other related polypeptides in the prior art.

Antibodies generated against polypeptides of the present invention may be obtained by administering the polypeptides or epitope-bearing fragments, analogs or cells to an animal, preferably a non-human animal, using routine protocols. For preparation of monoclonal antibodies, any technique which provides antibodies produced by continuous cell line cultures can be used. Examples include the hybridoma technique (Kohler, G. and Milstein, C., Nature (1975) 256:495–497), the trioma technique, the human B-cell hybridoma technique (Kozbor et al., Immunology Today (1983) 4:72) and the EBV-hybridoma technique (Cole et al., MONOCLONAL ANTIBODIES AND CANCER THERAPY, pp. 77–96, Alan R. Liss, Inc., 1985).

Techniques for the production of single chain antibodies, such as those described in U.S. Pat. No. 4,946,778, can also be adapted to produce single chain antibodies to polypeptides of this invention. Also, transgenic mice, or other organisms, including other mammals, may be used to express humanized antibodies.

The above-described antibodies may be employed to isolate or to identify clones expressing the polypeptide or to purify the polypeptides by affinity chromatography.

In a further aspect, the present invention relates to genetically engineered soluble fusion proteins comprising a polypeptide of the present invention, or a fragment thereof, and various portions of the constant regions of heavy or light chains of immunoglobulins of various subclasses (IgG, IgM, IgA, IgE). Preferred as an immunoglobulin is the constant part of the heavy chain of human IgG, particularly IgG1, where fusion takes place at the hinge region. In a particular embodiment, the Fc part can be removed simply by incorporation of a cleavage sequence which can be cleaved with blood clotting factor Xa. Furthermore, this invention relates to processes for the preparation of these fusion proteins by genetic engineering, and to the use thereof for, for example, drug screening.

Transgenic Cells and Mammals

The nucleic and amino acids of the invention can be used to produce recombinant cells and transgenic non-human mammals which are useful tools for the study of TIRAP function. That is, the exogenous nucleic acid, or transgene as it is also referred to herein, of the invention is introduced into a cell, and the cell is then used to generate the non-human transgenic mammal. The cell into which the transgene is introduced is preferably an embryonic stem (ES) cell. However, the invention should not be construed to be limited solely to ES cells comprising the transgene of the invention nor to cells used to produce transgenic animals. Rather, a transgenic cell of the invention includes, but is not limited to, any cell derived from a transgenic animal comprising a transgene, a cell comprising the transgene derived from a chimeric animal derived from the transgenic ES cell, and any other comprising the transgene which may or may not be used to generate a non-human transgenic mammal.

Further, it is important to note that the purpose of transgene-comprising, i.e., recombinant, cells should not be construed to be limited to the generation of transgenic mammals. Rather, the invention should be construed to include any cell type into which a nucleic acid encoding TIRAP is introduced, including, without limitation, a prokaryotic cell and a eukaryotic cell comprising an isolated nucleic acid encoding TIRAP.

When the cell is a eukaryotic cell, the cell may be any eukaryotic cell which, when the transgene of the invention is introduced therein, and the protein encoded by the desired gene is no longer expressed therefrom, a benefit is obtained. Such a benefit may include the fact that there has been provided a system in which lack of expression of the desired gene can be studied in vitro in the laboratory or in a mammal in which the cell resides, a system wherein cells comprising the introduced gene deletion can be used as research, diagnostic and therapeutic tools, and a system wherein animal models are generated which are useful for the development of new diagnostic and therapeutic tools for selected disease states in a mammal.

Alternatively, the invention includes a eukaryotic cell which, when the transgene of the invention is introduced therein, and the protein encoded by the desired gene is expressed therefrom where it was not previously present or expressed in the cell or where it is now expressed at a level or under circumstances different than that before the transgene was introduced, a benefit is obtained. Such a benefit may include the fact that there has been provided a system in the expression of the desired gene can be studied in vitro in the laboratory or in a mammal in which the cell resides, a system wherein cells comprising the introduced gene can be used as research, diagnostic and therapeutic tools, and a system wherein animal models are generated which are useful for the development of new diagnostic and therapeutic tools for selected disease states in a mammal.

Such cell expressing an isolated nucleic acid encoding TIRAP can be used to provide TIRAP to a cell, tissue, or whole animal where a higher level of TIRAP can be useful to treat or alleviate a disease, disorder or condition associated with low level of TIRAP expression and/or activity. Such diseases, disorders or conditions can include, but are not limited to, intestinal tumors, familial adenomatous polyposis, colon cancer, irritable bowel disease, inflammatory bowel disease, diabetes, obesity, tongue cancer, breast cancer, lung cancer, and the like. Therefore, the invention includes a cell expressing TIRAP to increase or induce TIRAP expression, translation, and/or activity, where increasing TIRAP expression, protein level, and/or activity can be useful to treat or alleviate a disease, disorder or condition.

One of ordinary skill would appreciate, based upon the disclosure provided herein, that a "knock-in" or "knock-out" vector of the invention comprises at least two sequences homologous to two portions of the nucleic acid which is to be replaced or deleted, respectively. The two sequences are homologous with sequences that flank the gene; that is, one sequence is homologous with a region at or near the 5' portion of the coding sequence of the nucleic acid encoding TIRAP and the other sequence is further downstream from the first. One skilled in the art would appreciate, based upon the disclosure provided herein, that the present invention is not limited to any specific flanking nucleic acid sequences. Instead, the targeting vector may comprise two sequences which remove some or all (i.e., a "knock-out" vector) or which insert (i.e., a "knock-in" vector) a nucleic acid encoding TIRAP, or a fragment thereof, from or into a mammalian genome, respectively. The crucial feature of the targeting vector is that it comprise sufficient portions of two sequences located towards opposite, i.e., 5' and 3', ends of the TIRAP open reading frame (ORF) in the case of a "knock-out" vector, to allow deletion/insertion by homologous recombination to occur such that all or a portion of the nucleic acid encoding TIRAP is deleted from or inserted into a location on a mammalian chromosome.

The design of transgenes and knock-in and knock-out targeting vectors is well-known in the art and is described in standard treatises such as Sambrook et al. (1989, Molecular Cloning: A Laboratory Manual, Cold Spring Harbor Laboratory, New York), and in Ausubel et al. (1997, Current Protocols in Molecular Biology, John Wiley & Sons, New York), and the like. The upstream and downstream portions flanking or within the TIRAP coding region to be used in the targeting vector may be easily selected based upon known methods and following the teachings disclosed herein based on the disclosure provided herein including the nucleic and amino acid sequences of both mouse and human TIRAP. Armed with these sequences, one of ordinary skill in the art would be able to construct the transgenes and knock-out vectors of the invention.

The invention further includes a knock-out targeting vector comprising a nucleic acid encoding a selectable marker such as, for example, a nucleic acid encoding the $neo^R$ gene thereby allowing the selection of transgenic a cell where the nucleic acid encoding TIRAP, or a portion thereof, has been deleted and replaced with the neomycin resistance gene by the cell's ability to grow in the presence of G418. However, the present invention should not be construed to be limited to neomycin resistance as a selectable marker. Rather, other selectable markers well-known in the art may be used in the knock-out targeting vector to allow selection of recombinant cells where the TIRAP gene has been deleted and/or inactivated and replaced by the nucleic acid encoding the selectable marker of choice. Methods of selecting and incorporating a selectable marker into a vector are well-known in the art and are describe in, for example, Sambrook et al. (1989, Molecular Cloning: A Laboratory Manual, Cold Spring Harbor Laboratory, New York), and in Ausubel et al. (1997, Current Protocols in Molecular Biology, John Wiley & Sons, New York).

As noted herein, the invention includes a non-human transgenic mammal comprising an exogenous nucleic acid inserted into a desired site in the genome thereof thereby deleting the coding region of a desired endogenous target gene, i.e., a knock-out transgenic mammal. Further, the invention includes a transgenic non-human mammal wherein an exogenous nucleic acid encoding TIRAP is inserted into a site the genome, i.e., a "knock-in" transgenic mammal. The knock-in transgene inserted may comprise various nucleic acids encoding, for example, a tag polypeptide, a promoter/regulatory region operably linked to the nucleic acid encoding TIRAP not normally present in the cell or not typically operably linked to TIRAP.

The generation of the non-human transgenic mammal of the invention is preferably accomplished using the method which is now described. However, the invention should in no way be construed as being limited solely to the use of this method, in that, other methods can be used to generate the desired knock-out mammal.

In the preferred method of generating a non-human transgenic mammal, ES cells are generated comprising the transgene of the invention and the cells are then used to generate the knock-out animal essentially as described in Nagy and Rossant (1993, In: Gene Targeting, A Practical Approach, pp. 146–179, Joyner ed., IRL Press). ES cells behave as normal embryonic cells if they are returned to the embryonic environment by injection into a host blastocyst or aggregate with blastomere stage embryos. When so returned, the cells have the full potential to develop along all lineages of the embryo. Thus, it is possible, to obtain ES cells, introduce a desired DNA therein, and then return the cell to the embryonic environment for development into mature mammalian cells, wherein the desired DNA may be expressed.

Precise protocols for the generation of transgenic mice are disclosed in Nagy and Rossant (1993, In: Gene Targeting, A Practical Approach, Joyner ed. IRL Press, pp. 146–179). and are therefore not repeated herein. Transfection or transduction of ES cells in order to introduce the desired DNA therein is accomplished using standard protocols, such as those described, for example, in Sambrook et al. (1989, Molecular Cloning: A Laboratory Manual, Cold Spring Harbor Laboratory, New York), and in Ausubel et al. (1997, Current Protocols in Molecular Biology, John Wiley & Sons, New York). Preferably, the desired DNA contained within the transgene of the invention is electroporated into ES cells, and the cells are propagated as described in Soriano et al. (1991, Cell 64:693–702).

Introduction of an isolated nucleic acid into the fertilized egg of the mammal is accomplished by any number of standard techniques in transgenic technology (Hogan et al., 1986, Manipulating the Mouse Embryo: A Laboratory Manual, Cold Spring Harbor, N.Y.). Most commonly, the nucleic acid is introduced into the embryo by way of microinjection.

Once the nucleic acid is introduced into the egg, the egg is incubated for a short period of time and is then transferred into a pseudopregnant mammal of the same species from which the egg was obtained as described, for example, in Hogan et al. (1986, Manipulating the Mouse Embryo: A Laboratory Manual, Cold Spring Harbor, N.Y.). Typically, many eggs are injected per experiment, and approximately two-thirds of the eggs survive the procedure. About twenty viable eggs are then transferred into pseudopregnant animals, and usually four to ten of the viable eggs so transferred will develop into live pups.

Any mammalian TIRAP gene may be used in the methods described herein to produce a transgenic mammal or a transgenic cell harboring a transgene comprising a deletion of all or part of that TIRAP gene. Preferably, human TIRAP polynucleotide (SEQ ID NO:1) or mouse TIRAP polynucleotide (SEQ ID NO:2) is also used.

The transgenic mammal of the invention can be any species of mammal. Thus, the invention should be construed to include generation of transgenic mammals encoding the chimeric nucleic acid, which mammals include mice, hamsters, rats, rabbits, pigs, sheep and cattle. The methods described herein for generation of transgenic mice can be analogously applied using any mammalian species. Preferably, the transgenic mammal of the invention is a rodent and even more preferably, the transgenic mammal of the invention is a mouse. By way of example, Lukkarinen et al. (1997, Stroke 28:639–645), teaches that gene constructs which enable the generation of transgenic mice also enable the generation of other transgenic rodents, including rats. Similarly, nullizygous mutations in a genetic locus of an animal of one species can be replicated in an animal of another species having a genetic locus highly homologous to the first species.

To identify the transgenic mammals of the invention, pups are examined for the presence of the isolated nucleic acid using standard technology such as Southern blot hybridization, PCR, and/or RT-PCR. Expression of the nucleic acid in the cells and in the tissues of the mammal is also assessed using ordinary technology described herein. Further, the presence or absence of TIRAP in the circulating blood of the transgenic animal can be determined, for example, as disclosed herein (e.g., Western blot analysis), or using standard methods for protein detection that are well-known in the art.

Cells obtained from the transgenic mammal of the invention, which are also considered "transgenic cells" as the term is used herein, encompass such as cells as those obtained from the TIRAP (+/−) and (−/−) transgenic non-human mammal described elsewhere herein, are useful systems for modeling diseases and symptoms of mammals which are believed to be associated with altered levels of TIRAP expression such as colon cancer, familial adenomatous polyposis, irritable bowel disease, inflammatory bowel disease, intestinal tumors, breast cancer, tongue cancer, diabetes, and obesity, and any other disease, disorder or condition associated with an altered level of TIRAP expression. Moreover, as a marker of a pathway(s) associated with tumor proliferation and other intestinal abnormalities such colon cancer, familial adenomatous polyposis, irritable bowel disease, inflammatory bowel disease, intestinal tumors, breast cancer, tongue cancer, diabetes, and obesity, TIRAP expression levels are also useful indicators in assessment of such diseases, disorders or conditions.

Particularly suitable are cells derived from a tissue of the non-human knock-out or knock-in transgenic mammal described herein, wherein the transgene comprising the TIRAP gene is expressed or inhibits expression of TIRAP in various tissues. By way of example, cell types from which such cells are derived include fibroblasts, endothelial, adipocyte, and myoblast cells of (1) the TIRAP (+/+), (+/−) and (−/−) non-human transgenic liveborn mammal, (2) the TIRAP (+/+), (−/−) or (+/−) fetal animal, and (3) placental cell lines obtained from the TIRAP (+/+), (−/−) and (+/−) fetus and liveborn mammal.

The following definitions are provided to facilitate understamiding of certain terms used frequently hereinbefore.

"Antibodies" as used herein includes polyclonal and monoclonal antibodies, chimeric, single chain, and humanized antibodies, as well as Fab fragments, including the products of an Fab or other immunoglobulin expression library.

"Identity," as known in the art, is a relationship between two or more polypeptide sequences or two or more polynucleotide sequences, as the case may be, as determined by comparing the sequences. In the art, "identity" also means the degree of sequence relatedness between polypeptide or polynucleotide sequences, as the case may be, as determined by the match between strings of such sequences. "Identity" can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, 30 H., and Lipman, D., SIAM J. Applied Math., 48: 1073 (1988). Methods to determine identity are designed to give the largest match between the sequences tested. Moreover, methods to determine identity are codified in publicly available computer programs. Computer program methods to determine identity between two sequences include, but are not limited to, the GCG program package (Devereux, J., et al., Nucleic Acids Research 12(1): 387 (1984)), BLASTP, BLASTN, and FASTA (Atschul, S. F. et al., J Molec. Biol. 215: 403–410 (1990). The BLAST X program is publicly available from NCBI and other sources (BLASTManual, Altschul, S., et al, NCBI NLM NIH Bethesda, Md. 20894, Altschul, S., et al., J. Mol. Biol. 215: 403–410 (1990). The well-known Smith Waterman algorithm may also be used to determine identity.

Parameters for polypeptide sequence comparison include the following:

1) Algorithm: Needleman and Wunsch, J. Mol. Biol. 48: 443–453 (1970)

Comparison matrix: BLOSSUM62 from Hentikoff and Hentikoff, Proc. Natl. Acad. Sci. USA. 89:10915–10919 (1992)

Gap Penalty: 12

Gap Length Penalty: 4

A program useful with these parameters is publicly available as the "gap" program from Genetics Computer Group, Madison Wis. The aforementioned parameters are the default parameters for peptide comparisons (along with no penalty for end gaps). Parameters for polynucleotide comparison include the following:

1) Algorithm: Needleman and Wunsch, J. Mol. Biol. 48: 443–453 (1970)

Comparison matrix: matches=+10, mismatch=0

Gap Penalty: 50

Gap Length Penalty: 3

Available as: The "gap" program from Genetics Computer Group, Madison Wis. These are the default parameters for nucleic acid comparisons.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

"Polynucleotide" generally refers to any polyribonucleotide or polydeoxribonucleotide, which may be unmodified RNA or DNA or modified RNA or DNA.

"Polynucleotides" include, without limitation, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term "polynucleotide" also includes DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques which are well known in the art. Such modifications are well described in basic texts and in more detailed monographs, as well as in a voluminous research literature. Modifications may occur anywhere in a polypeptide, including the peptide backbone, the amino acid side-chains and the amino or carboxyl termini. It will be appreciated that the same type of modification may be present to the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from post-translation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination (see, for instance, PROTEINS— STRUCTURE AND MOLECULAR PROPERTIES, 2nd Ed., T. E. Creighton, W. H. Freeman and Company, New York, 1993; Wold, F., Post-translational Protein Modifications: Perspectives and Prospects, pgs. 1–12 in POST-TRANSLATIONAL COVALENT MODIFICATION OF PROTEINS, B. C. Johnson, Ed., Academic Press, New York, 1983; Seifter et al., "Analysis for protein modifications and nonprotein cofactors", Meth Enzymol (1990) 182:626–646 and Rattan et al., "Protein Synthesis: Post-translational Modifications and Aging", Ann NY Acad Sci (1992) 663:48–62).

"Small Molecule" or "Small Molecule Compound" refers to a synthetic organic compound that is typically less than about 2 kilodaltons (KD).

The term "transgene" is used herein to describe genetic material that has been or is about to be artificially inserted into the genome of a mammalian cell, particularly a mammalian cell of a living animal. The transgene is used to transform a cell, meaning that a permanent or transient genetic change, preferably a permanent genetic change, is induced in a cell following incorporation of exogenous DNA. A permanent genetic change is generally achieved by introduction of the DNA into the genome of the cell. Vectors for stable integration include plasmids, retroviruses and other animal viruses, YACs, and the like. Of interest are transgenic mammals, e.g. cows, pigs, goats, horses, etc., and particularly rodents, e.g. rats, mice, etc.

Transgenic animals include an exogenous nucleic acid sequence present as an extrachromosomal element or stably integrated in all or a portion of its cells, especially in germ cells. Unless otherwise indicated, it will be assumed that a transgenic animal includes stable changes to the germline sequence. During the initial construction of the animal, "chimeras" or "chimeric animals" are generated, in which only a subset of cells have the altered genome. Chimeras are primarily used for breeding purposes in order to generate the desired transgenic animal. Animals having a heterozygous alteration are generated by breeding of chimeras. Male and female heterozygotes are typically bred to generate homozygous animals.

In the present invention, "knock-outs" have a partial or complete loss of function in one or both alleles of the endogenous gene of interest, as opposed to "knock-ins" which have an introduced transgene with altered genetic sequence and function from the endogenous gene. The two may be combined, such that the naturally occurring gene is disabled, and an altered form introduced. In a knock-out, preferably the target gene expression is rendered undetectable or insignificant. A knock-out of a TIRAP gene means that function of TIRAP has been substantially decreased so that expression is not detectable or only present at insignificant levels. This may be achieved by a variety of mechanisms, including introduction of a disruption of the coding sequence, e.g. insertion of one or more stop codons, insertion of a DNA fragment, etc., deletion of coding sequence, substitution of stop codons for coding sequence, etc. In some cases the exogenous transgene sequences are ultimately deleted from the genome, leaving a net change to the native sequence. Different approaches may be used to achieve the knock-out. A chromosomal deletion of all or part of the native gene may be induced, including deletions of the non-coding regions, particularly the promoter region, 3' regulatory sequences, enhancers, or deletions of gene that activate expression of genes. A functional knock-out may also be achieved by the introduction of an anti-sense construct that blocks expression of the native genes (for example, see Li and Cohen (1996) Cell 85:319–329). Knock-outs also include conditional knock-outs, for example where alteration of the target gene occurs upon exposure of the animal to a substance that promotes target gene alteration, introduction of an enzyme that promotes recombination at the target gene site (e.g. Cre in the Cre-lox system), or other method for directing the target gene alteration postnatally.

All publications, including but not limited to patents and patent applications, cited in this specification are herein incorporated by reference as if each individual publication were specifically and individually indicated to be incorporated by reference herein as though fully set forth.

The invention is further described in detail be reference to the following experimental examples. These examples are provided for purposed of illustration only, and are not intended to be limiting unless otherwise specified. Thus, the invention should in no way be construed as being limited to the following examples, but rather, should be construed to encompass any and all variations which become evident as a result of the teaching provided herein.

EXAMPLES

Example 1

TIRAP is a Component of the TLR4 Signaling Pathway, but not of the IL-1R Signaling Pathways To determine the effect of various TIRAP constructs on the promoter activity of NF-κB, 293T cells were co-transfected with 2.0 µg of the indicated TIRAP construct and 0.1 µg of an NF-κB-dependent luciferase reporter gene. pcDNA3 is an empty vector control; TIRAP is a vector encoding the full length TIRAP protein; TIRAP N is a vector encoding the N-terminal domain of TIRAP; TIRAP C is a vector encoding the C terminal domain of TIRAP; and TIRAP P125H is a vector encoding a mutant form of TIRAP containing a proline to histidine mutation at amino acid position 125. Cells were harvested 24 h post-transfection and lysed for analysis in a standard luciferase reporter assay. Luciferase activity is expressed as fold induction relative to mock transfected cells (FIG. 2A). Whereas the TIRAP construct resulted in strong activation of the NF-κB promoter (approximately 80-fold induction of luciferase activity); no significant promoter activity was observed in the presence of TIRAP N, TIRAP C, or TIRAP P125H. Based on these results, full length TIRAP, but not the mutant forms of TIRAP tested, activates the NF-κB promoter. These results further suggest that TIRAP is a component of the TLR4 signaling pathway.

Figure 2B:
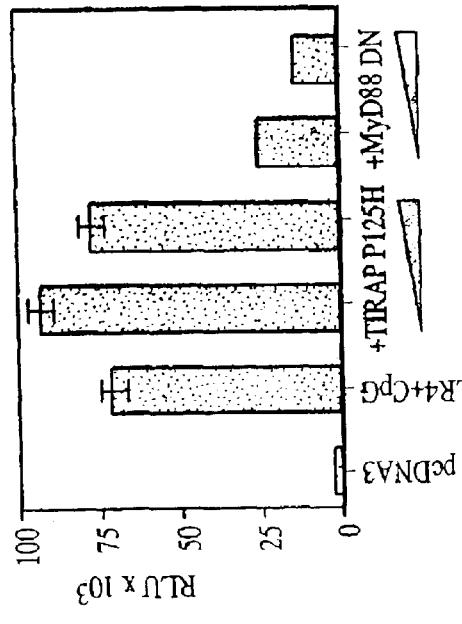

To determine whether TIRAP P125H functions as a dominant negative, 293T cells were transfected with 0.25 µg of vector alone (pcDNA3) or CD4/TLR4 (a vector expressing a constitutively active form of TLR4) with or without increasing concentrations (50 ng, 250 ng, 1.0 µg) of either TIRAP P125H or MyD88 DN (a vector expressing MyD88 containing a proline to histidine mutation at the same position as TIRAP P125H) and the NF-κB-dependent luciferase reporter gene. Interestingly, TIRAP P125H strongly inhibited activation of NF-κB mediated by CD4/TLR4 (FIG. 2B). This inhibition was dose-dependent and comparable to the inhibition of CD4/TLR4 by MyD88 DN. These results suggest that TIRAP P125H inhibits TLR4-mediated NF-κB activation. Notably, a MyD88 mutation at the same position can still activate NF-κB when overexpressed, indicating that there may be differences in the function of the TIRAP and MyD88 TIR domains.

Figure 2C:
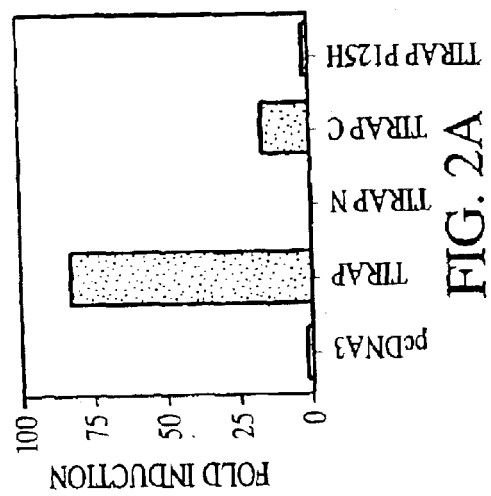

Unlike TLR4, neither IL-1R nor TLR9 can induce NF-κB in the absence of MyD88 (Kawai 1999; Schnare 2000; Adache 1998). To assess the possibility that TIRAP is the putative adapter in the MyD88-independent signaling pathway, we tested TIRAP P125H for its ability to inhibit NF-κB activity induced y IL-1R and TLR9. 293T cells were co-transfected with either vector alone (pcDNA3), IL-1R (0.1 µg), and IL-1R AcP (0.1 µg) [Dr. Medzhitov: Please indicate what the IL-1R AcP construct encodes] plasmid cDNAs, with or without increasing concentrations (10 ng, 50 ng, 200 ng) of TIRAP P125H plasmid and the NF-κB-dependent luciferase reporter gene. TIRAP P125H did not inhibit NF-κB activity induced either by co-transfected IL-1R and IL-1R AcP (FIG. 2C) or by IL-1B cytokine.

Figure 2D:
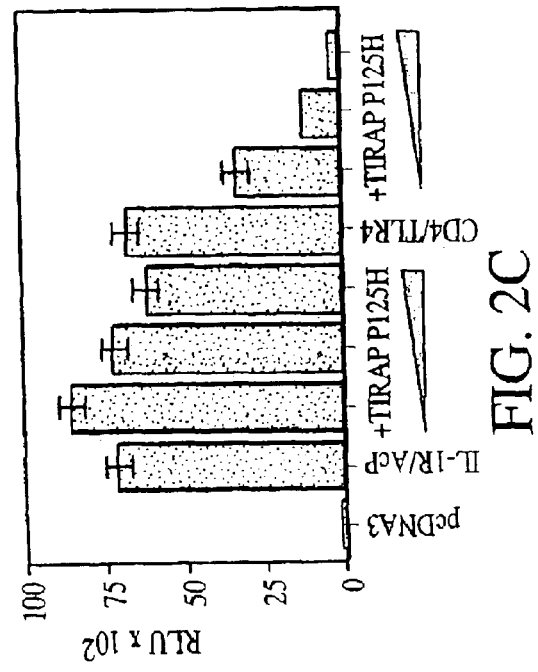

TLR9 does not induce NF-κB activity when overexpressed, but does so upon addition of its ligand CpG DNA. To determine whether TIRAP inhibits NF-κB activation induced by CpG-stimulation of TLR9-transfected cells, 293T cells were transfected with vector alone (pcDNA3), TLR9 (50 ng), with or without increasing concentrations (100 ng, 250 ng) of either TIRAP P125H or MyD88 DN. At twenty-four h post transfection, CpG oligonucleotides were added at 3 µM final concentration to TLR9-transfected samples and incubated for 14 more hours before harvesting. Whereas MyD88 DN inhibited CpG signaling, consistent with the ability of CpG DNA to activate NF-κB in MyD88-deficient cells (Schnare 2000), TIRAP P125H did not inhibit NF-κB activation induced by CpG-stimulation of TLR9-transfected cells (FIG. 2D). Thus, TIRAP appears to function downstream of TLR4 but not IL-1R or TLR9, and is likely to be the adapter in the MyD88-independent pathway downstream of TLR4.

Example 2

Wild-type TIRAP but not TIRAP P125H Co-Immunoprecipitates with TLR4

Figure 3A:
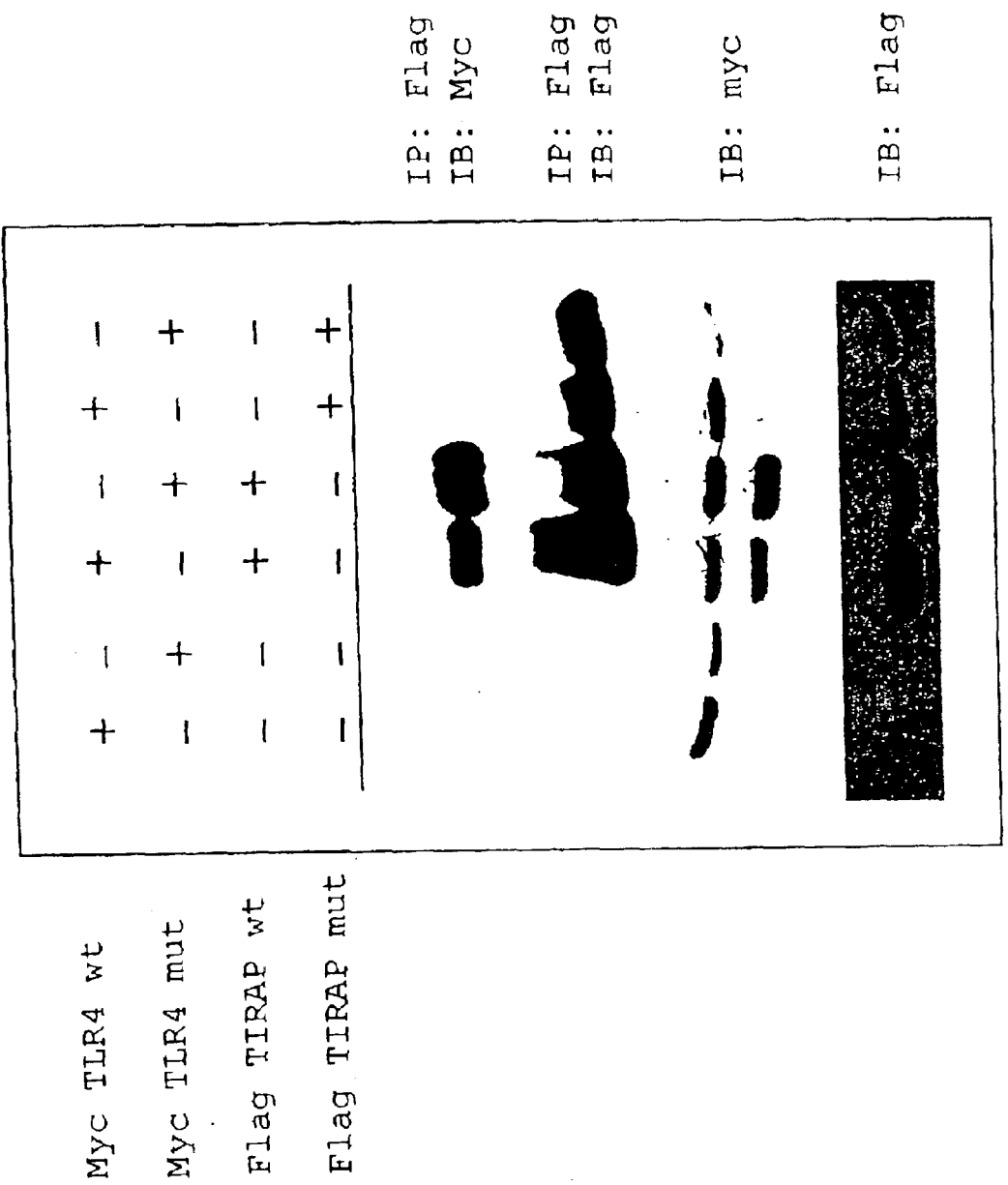
FIGS. 3A and 3B, is a pair of images of immunoblots demonstrating co-immunoprecipitation of TIRAP with TLR4 and MyD88. Cells were transfected in the presence (+) or absence (−) of constructs encoding a wild-type portion of TLR4 (TLR4 wt), a mutant derivative thereof (TLR4 mut), wild-type TIRAP (TIRAP), a mutant TIRAP containing a P125H mutation (TIRAP PH), or wild-type MyD88 (MyD88), wherein each construct further encodes a Myc, Flag, or hemaglutanin (HA) tag, as indicated. Antibodies used for immunoprecipitation (IP) or immunoblot (IB) are indicated to the left of each blot.

To obtain biochemical conformation for a role of TIRAP in the TLR4 signaling pathway, TIRAP-TLR4 protein interactions were evaluated using co-immunoprecipitation experiments. 293T cells were co-transfected with 4.5 µg of a Myc-tagged TLR4 deletion construct lacking the ectodomain (Myc TLR4 wt) or its mutant derivative (Myc TLR4 P714H) in the presence or absence of 1.5 µg of Flag-tagged TIRAP (Flag TIRAP) or its mutant derivative containing the P125H mutation (Flag TIRAP PH). Lysates prepared 24 h post-transfection were incubated overnight with anti-Flag M2 agarose beads to immunoprecipitate Flag TIRAP or Flag TIRAP P125H and any associated proteins. Immunocomplexes were washed, separated by SDS-PAGE electrophoresis, and then analyzed by immunoblotting with either anti-myc antibody to look for co-immunoprecipitated TLR4 or anti-Flag antibody to confirm immunoprecipitation of Flag TIRAP or Flag TIRAP P125H. Total cell lysates (35 µg/sample) were likewise analyzed by SDS-PAGE and immunoblotting to confirm equivalent expression of the appropriate proteins in every sample. These experiments revealed that TLR4 does in fact co-immunoprecipitate with TIRAP (FIG. 3A). The TLR4 mutant, TLR4 P714H, which cannot signal as a result of the mutation and thus, renders c3H/HeJ mice unresponsive to LPS, also co-immunoprecipitates with TLR4. In contrast, TIRAP P125H filed to co-immunoprecipitate with TLR4, suggesting that this conserved region of the TIR domain mediates interaction of TIRAP with the TIR domain of TLR4 (FIG. 3A).

Figure 3B:
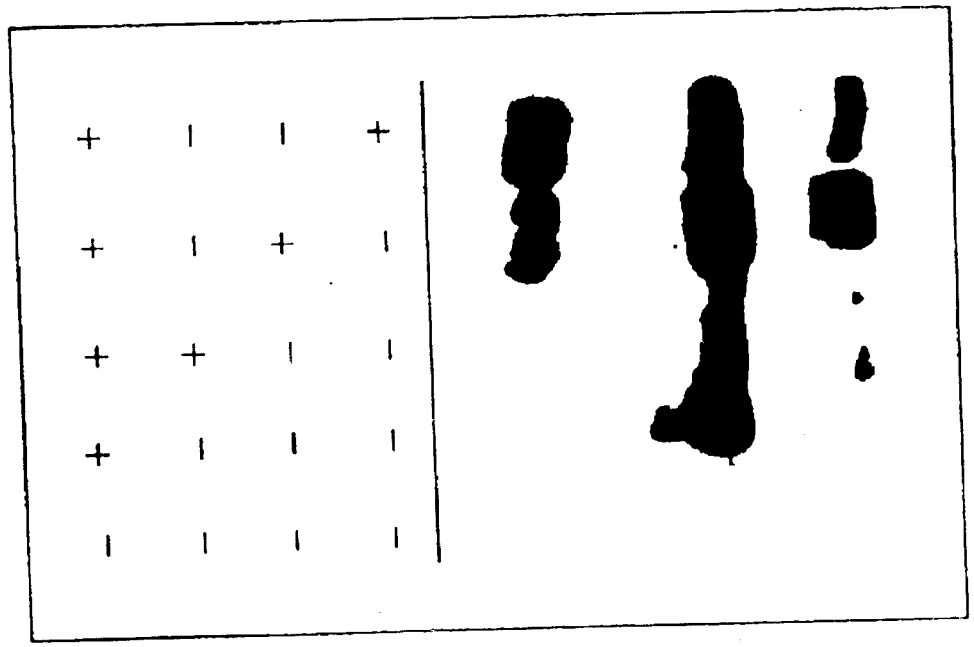

Similarly, the interaction between TIRAP and MyD88 was examined. 293T cells were transfected with 1.5 µg of either HA-tagged TIRAP (HA TIRAP) alone or in combination with 1.5 µg of either Flag-tagged MyD88 (Flag MyD88), Flag-tagged TIRAP (Flag-TIRAP), or Flag-tagged TIRAP P125H (Flag TIRAP PH). Immunoprecipitation and analyses of immunocomplexes as well as total cell lysates were done as described above. It was demonstrated that TIRAP does not interact with MyD88 (FIG. 3B), demonstrating the specificity of the TIR domain interactions detected by these assays. TIRAP also failed to associate with IRAK [Dr. Medzhitov: Please spell this out], suggesting that TIRAP may not have any role in the MyD88-dependent signaling pathway. However, TIRAP can be co-immunoprecipitated with itself (FIG. 3B), indicating that TIRAP can homodimerize, as is the case with many other TIR domain-containing proteins including TLR4 and MyD88. Direct interactions between TIRAP and the TIR domain of TLR4 was also detected using in vitro glutathione S transferase (GST) pull-down assays.

Example 3

Figure 4A:
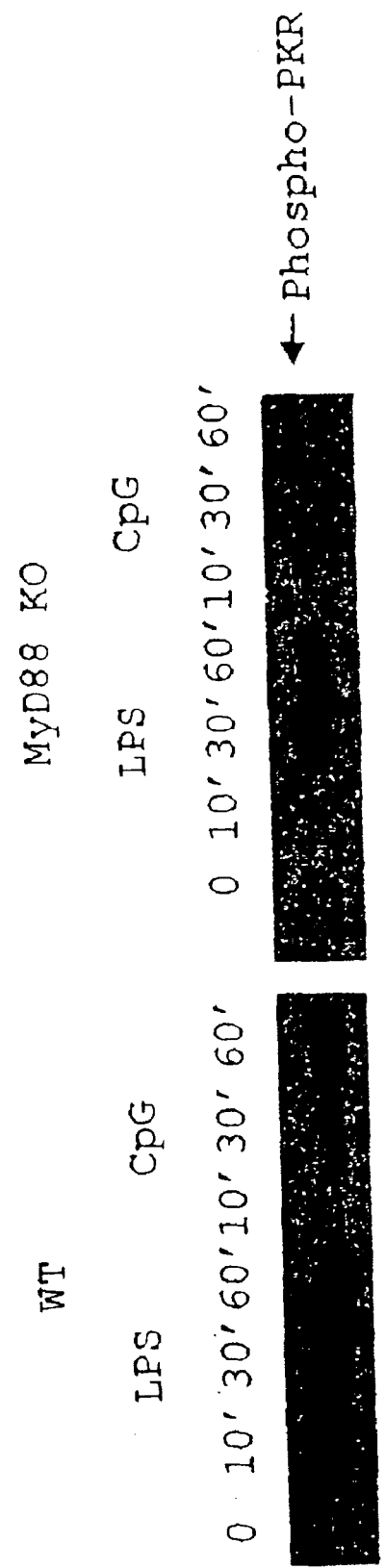
FIGS. 4A through 4C, is a series of images of immunoblots demonstrating that PKR co-immunoprecipitates with TIRAP and is a component of LPS and CpG-signaling pathways. (A) Bone marrow-derived macrophages from either wild-type (WT) or MyD88-deficient (MyD88$^{-/-}$) mice were stimulated for the indicated time periods (minutes) with either LPS or CpG, and immunoblots were performed using an antibody that specifically recognizes phosphorylated PKR (PKR-P). B and C Cells were transfected with constructs encoding Flag-tagged TIRAP and either a construct encoding an HA-tagged kinase dead mutant of PKR (HA PKR KD) or p58, as indicated. Antibodies used for immunoprecipitation (IP) or immunoblot (IB) are indicated to the left of each blot, and arrows on the right show the location of the indicated proteins.

PKR is a Component of LPS and CpG-Signaling Pathways, and Co-Immunoprecipitates with TIRAP It was recently demonstrated that cells lacking the interferon-regulated, dsRNA-binding protein kinase, PKR, fail to activate JNK and p38 in response to LPS stimulation (Goh 2000). As TLR4 is required for all signals downstream of LPS, this results report suggested that PKR is a component of the TLR4 signaling pathway. To determine whether PKR functions in the MyD88-dependent or -independent pathway, PKR activation was evaluated in wild-type and MyD88-deficient macrophages following LPS stimulation. To this end, bone marrow-derived macrophages from either wild-type or MyD88-deficient mice were stimulated for the indicated time periods with either LPS (10 ng/ml) or CpG (10 μM), then washed in PBS and lysed in TNT lysis buffer. Because PKR is phosphorylated on a threonine residue upon activation, activation of PKR was assayed by immunoblotting lysates (40 μg/sample), resolved by SDS-PAGE electrophoresis, with an antibody that specifically recognizes phosphorylated PKR. Activated, phosphorylated PKR was detectable in LPS-stimulated wild-type macrophages (FIG. 4A). Interestingly, phosphorylated PKR was also detected in LPS-stimulated MyD88-deficient macrophages, although a significantly smaller fraction of PKR is phosphorylated in these cells. In addition, MyD88-deficient cells activate PKR with slower kinetics, similar to the delayed kinetics of NF-κB and JNK activation. These observations strongly suggest that, in response to LPS stimulation, PKR is activated by MyD88-dependent as well as MyD88-independent mechanisms. If the MyD88-dependent pathway can activate PKR in response to LPS, it is conceivable that PKR may be activated by other TLRs. Therefore, PKR activation in response to CpG stimulation was tested. Indeed, PKR is phosphorylated in response to CpG (FIG. 4A), indicating that PKR is a component of the TLR9 pathway as well as the TLR4 pathway.

Figure 4B:
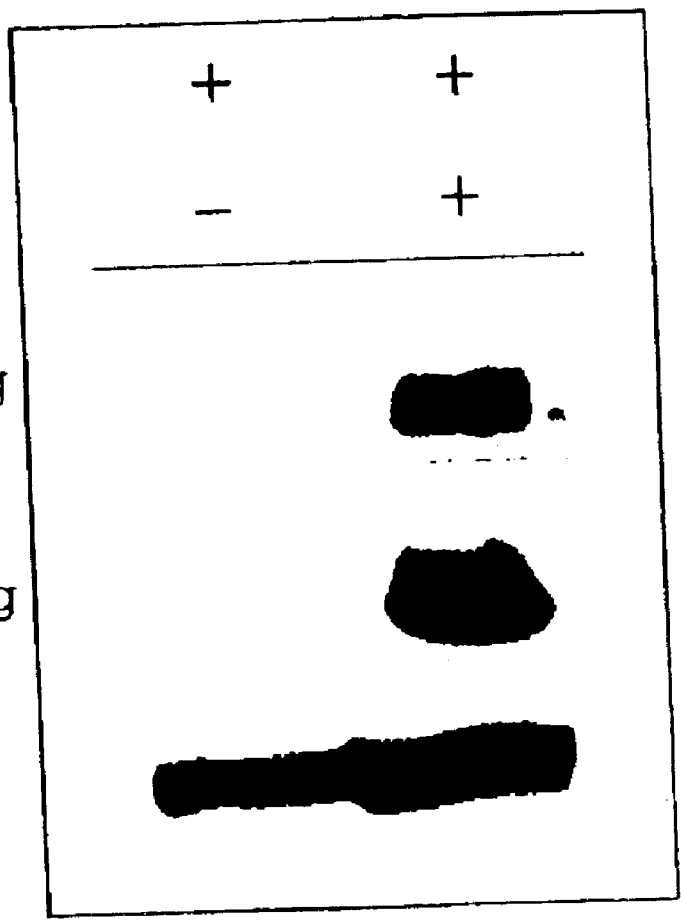

To determine whether PKR and TIRAP interact, lysates from 293T cells transfected with either 3.5 μg of an HA PKR kinase dead (KD) mutant or 1.5 μg of Flag TIRAP were subjected to immunoprecipitation analyses as described above, followed by SDS-PAGE and immunoblotting with the indicated antibodies. The PKR KD mutant rather than wild type PKR was used because overexpressing PKR induces cell death. PKR did, in fact, co-immunoprecipitate with TIRAP (FIG. 4B), further supporting the link between PKR and TIRAP established above.

Figure 4C:
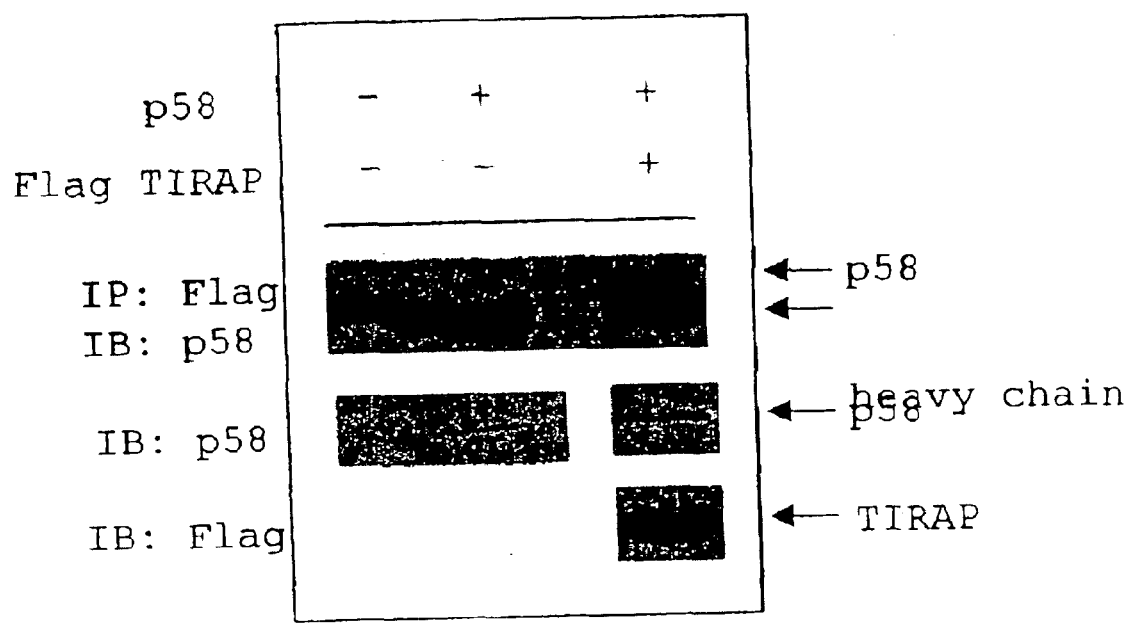

Because TIRAP may not regulate PKR directly, the interaction between TIRAP and two other proteins, p58 and PACT, was analyzed. p58 is a tetratricopeptide repeat-containing protein that negatively regulates PKR activity (Lee 1994), and PACT is a dsRNA-binding domain-containing protein that activates PKR in response to cellular stress (Patel 19980). Lysates from 293T cells transfected with either p58-encoding vector (3.5 μg) or PACT (3.5 μg) and Flag TIRAP (1.5 μg) were subject to immunoprecipitation analyses followed by SDS-PAGE and immunoblotting with the indicated antibodies. TIRAP was shown to immunoprecipitate with both p58 and PACT (FIG. 4C), indicating that PKR and/or its regulators p58 and PACT may be downstream targets of TIRAP.

Example 4

Figure 5A:
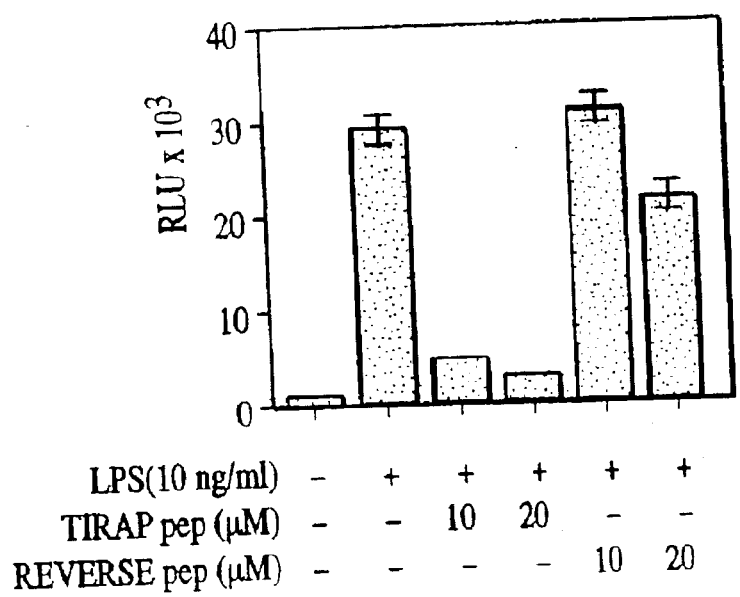

The Cell Permeable TIRAP Inhibitory Peptide Inhibits LPS but not CpG Induced NF-κB Activation, PKR Phosphorylation, and JNK Phosphorylation To further elucidate the function of TIRAP, alternative methods of TIRAP inhibition were sought. The fact that the TIRAP P125H mutant functioned as a dominant negative and could no longer interact with TLR4 indicated that the mutated residue is critical for TIRAP activity, including its ability to interact with the upstream receptor. Therefore, a peptide corresponding to this region of wild-type TIRAP may act as a site-specific inhibitor of TIRAP by competing with TIRAP for interaction with TLR4. To test this possibility, a cell-permeable peptide, useful for cellular assays, was first constructed. A synthetic peptide corresponding to this region of mTIRAP was linked to the C-terminus of a peptide derived from antennapedia. The antennapedia peptide can cross cell membranes when added exogenously to cell cultures, and serves as a vehicle to deliver the fusion peptide into the cell (Derossi 1998). A RAW macrophage cell line stably transfected with an NF-κB-dependent luciferase reporter gene (RAW κB) was pretreated for 1 hour with the indicated concentrations of either the TIRAP inhibitory peptide or 50 μM of control peptide, then stimulated for 5 hours with LPS (10 ng/ml) before harvesting for the reporter assay. Samples were treated and stimulated in duplicates. Pretreatment of the RAW κB cell line with the TIRAP peptide potently inhibited LPS-induced NF-κB activation (FIG. 5A). However, no effect on NF-κB activation was observed upon pretreatment with either the solvent, DMSO, or a control peptide in which the TIRAP sequence was reversed (FIG. 5A).

To determine the effect of TIRAP on IκB-α degradation, the following experiment was performed. RAW cells, either untreated or pretreated for 1 hour with 40 μM of the TIRAP peptide, were either left unstimulated or stimulated with LPS (10 ng/ml) for the indicated time periods before harvesting for lysis in TNT lysis buffer. Lysates (30 μg/sample) were resolved by SDS-PAGE electrophoresis followed by immunoblotting with an anti-IκB-α degradation. Consistent with the block in NF-κB activation demonstrated above, LPS stimulation did not induce IκB-α degradation in RAW cells pretreated with the TIRAP peptide (FIG. 5B).

Figure 5C:
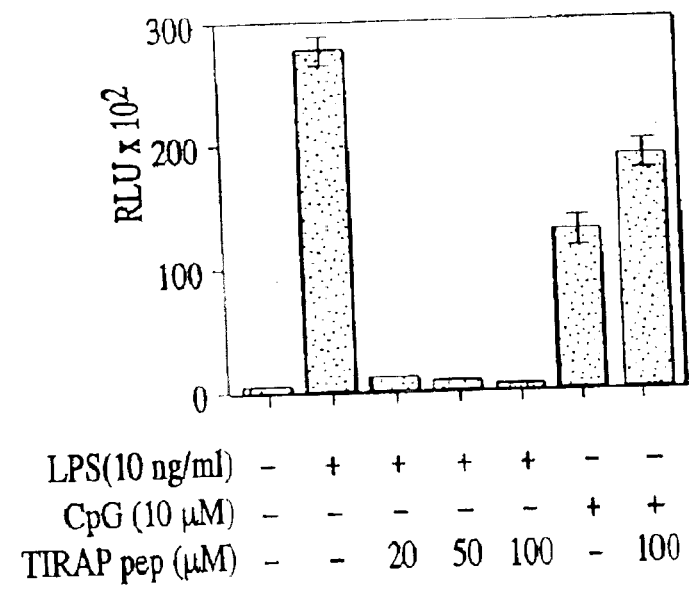

To determine whether a TIRAP mutant peptide inhibits CpG-stimulated signaling, RAW κB cells were pretreated with the indicated concentrations of the TIRAP peptide and stimulated for 5 hours with either LPS (10 ng/ml) or CpG (10 μM) before harvesting for reporter assay. Importantly, pretreatment of RAW cells with the TIRAP peptide did not inhibit either CpG-induced NF-κB activation (FIG. 5C) or CpG-induced IκB-α degradation, nor did the peptide inhibit NF-κB activation mediated by IL-1B cytokine in 293 cells.

To determine whether a TIRAP mutant peptide inhibits PKR and JNK phosphorylation induced by LPS or CpG, RAW cells either untreated or pretreated with 40 μM of the TIRAP peptide were either left unstimulated or stimulated with either LPS (10 ng/ml) or CpG (10 μM) for the indicated time periods before harvest and lysis. Lysates (30 μg/sample) were analyzed by SDS-PAGE followed by immunoblotting with antibodies that specifically recognize phosphorylated PKR and JNK. Furthermore, the TIRAP peptide, but not the control peptide, also inhibited PKR phosphorylation induced by LPS, but not CpG, in RAW cells (FIG. 5D), supporting the possibility that PKR functions downstream of TIRAP.

These data are consistent with the results from transient transfection assays which utilized the TIRAP P125H dominant negative construct, and they strongly support the hypothesis that TIRAP functions downstream of TLR4, but not TLR9 or IL-1R. Moreover, the fact that the TIRAP peptide does not inhibit CpG-induced effects rules out the possibility that the TIRAP peptide inhibits LPS signaling by causing cytotoxicity or by interfering non-specifically with other cellular processes.

Example 5

TIRAP Controls Dendritic Cell Maturation

Figure 6A:
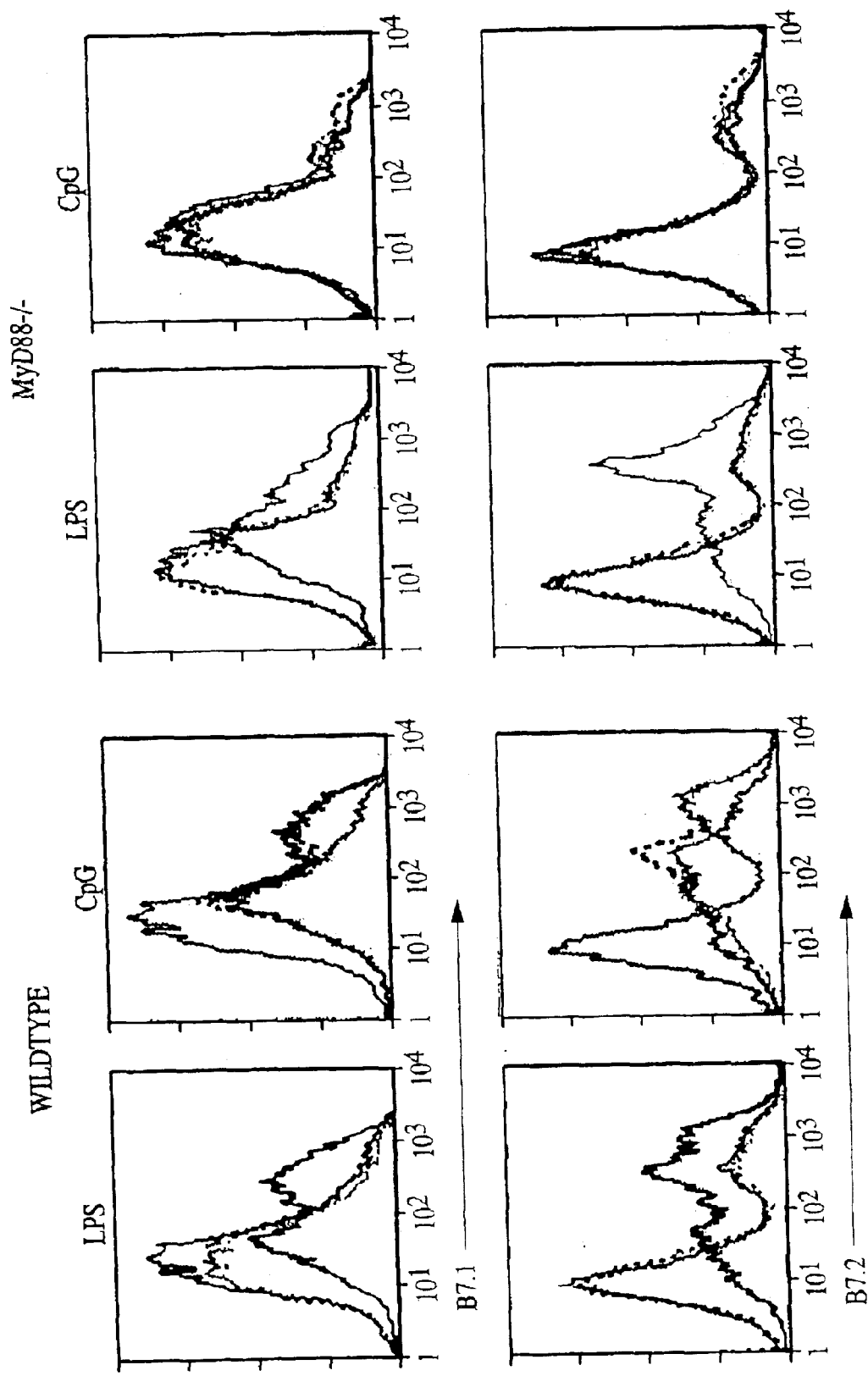
FIGS. 6A through 6C, is a series of graphs indicating that TIRAP induces dendritic cell maturation. (A) Wild-type and MyD88$^{-/-}$ dendritic cells (DCs) were induced with LPS or CpG and analyzed for expression of the costimulatory molecules B7.1 and B7.1 using flow cytometry. (B) Production of the cytokines, IL-12 and IL-6, was measured in cells that were untreated (none) or treated with LPS or CpG in the presence or absence of TIRAP peptide. (C) T cell proliferation was measured in wild-type DCs that were untreated (none), treated with LPS alone (LPS), or treated with LPS in the presence of increasing amounts of TIRAP peptide (LPS+TIRAP peptide). T cell proliferation was measured by incorporation of $^3$H-thymidine into cells, expressed as cpm×10$^3$.

In view of the important role for TIRAP in mediating LPS-responsiveness in macrophages, the role of TIRAP in LPS-induced DC maturation was investigated. TIRAP is likely to be critical in these events because MyD88-deficient DCs retain the ability to upregulate costimulatory molecules in response to LPS stimulation (Kaisho 2001). To determine the effect of TIRAP on the expression of the costimulatory molecules B7.1 and B7.2, flow cytometry was performed on wild type and MyD88-/-DC. DCs were either unstimulated (shaded), stimulated with LPS (10 ng/ml) or CpG (10 µM) (black line), or pretreated with TIRAP peptide (10 µM) prior to stimulation with LPS or CpG (dashed line). Indeed, the TIRAP peptide abolished LPS-induced upregulation of B7.1 and B7.2 molecules in both wild-type and MyD88-deficient DCs (FIG. 6A). However, the peptide had no effect on CpG-induced DC maturation (FIG. 6A).

Figure 6B:
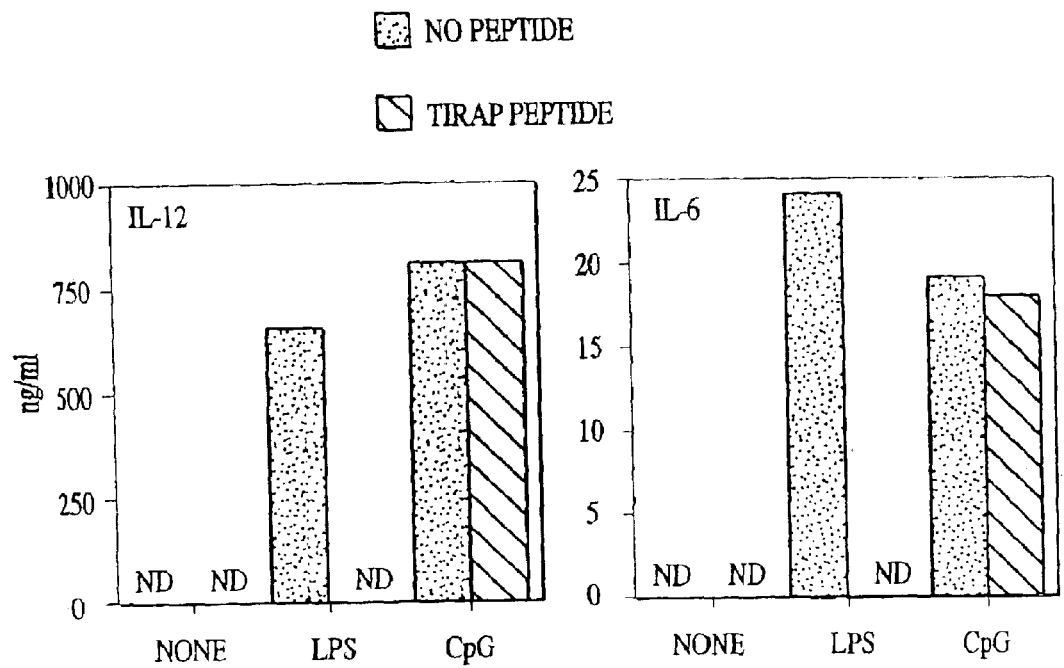

To determine the effects of the TIRAP peptide on cytokine production, DCs were treated with or without TIRAP peptide prior to stimulation with LPS or CpG (as described above), and the production of IL-12 and IL-6 was measured. Addition of TIRAP peptide inhibited production of IL-12 and IL-6 cytokines in response to stimulation with LPS, but not CpG (FIG. 6B).

Figure 6C:
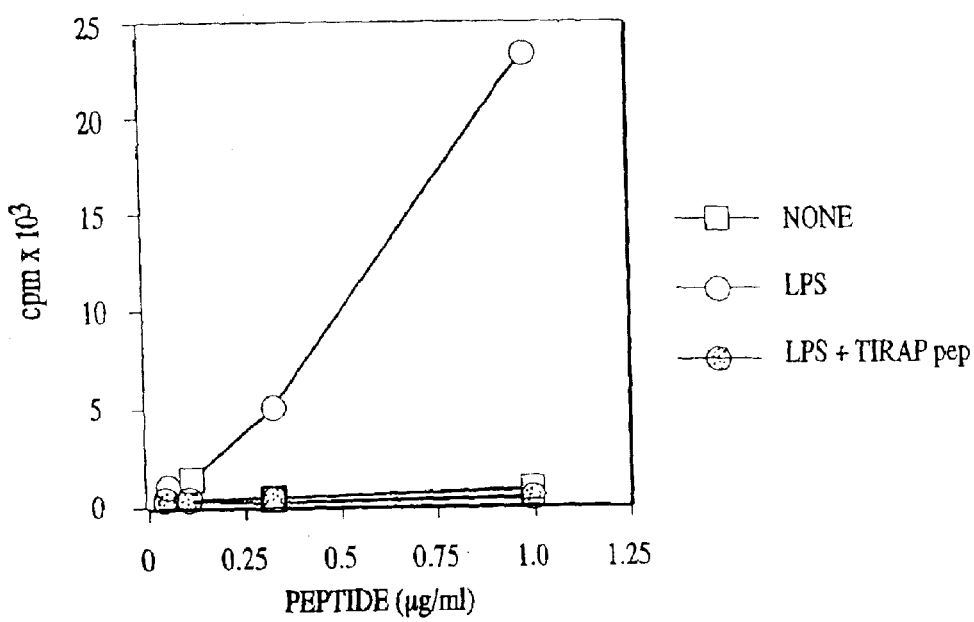
Figure 7:
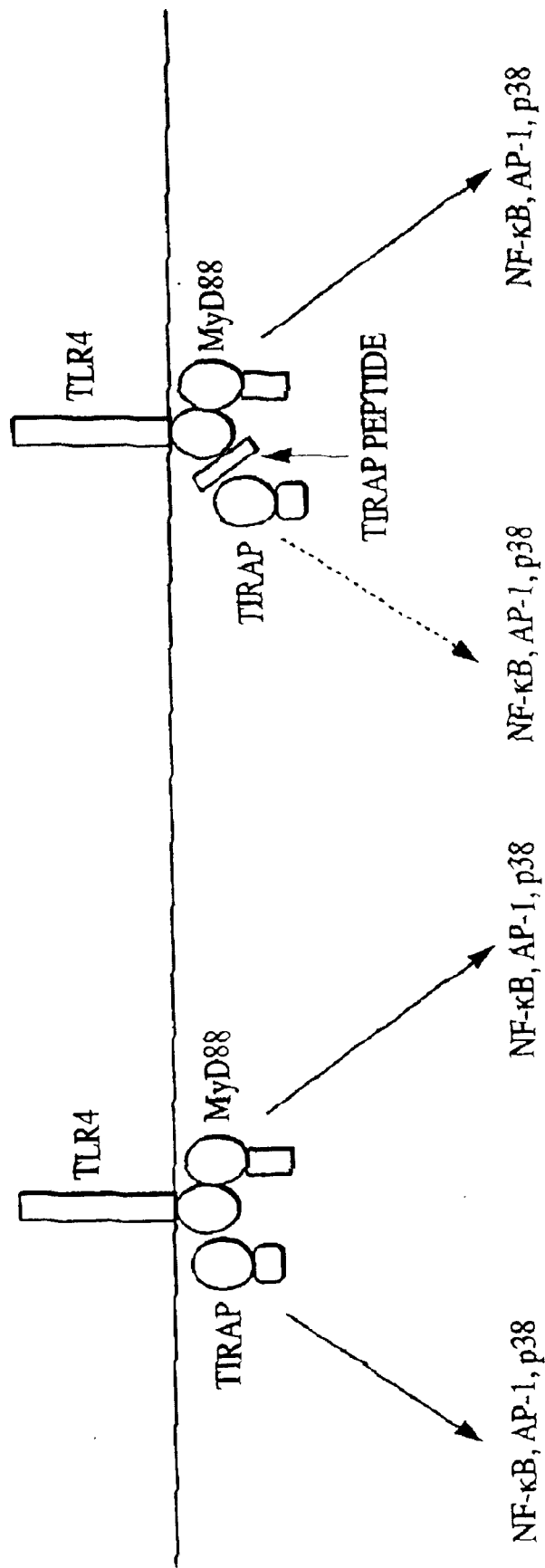
FIG. 7 is a diagram depicting a proposed mechanism for the function of TIRAP and an inhibitory TIRAP peptide. The horizontal black line differentiates the extracellular space (above the line) from the intracellular space (below the line). TLR4, TIRAP, MyD88, and an inhibitory TIRAP peptide are shown schematically. Solid arrows indicate activation of the indicated proteins (NF-κB, AP-1, and p38), whereas a dotted line indicates that activation of these proteins is inhibited.

Lastly, the effect of TIRAP peptide on T cell proliferation was evaluated. Stimulation of CD4 T cell proliferation by DCs treated with or without TIRAP peptide prior to stimulation with LPS was performed in the presence of varying concentrations of Eα peptide. DCs were fixed prior to incubation with 1H3.1 TCR transgenic T cells (specific for Eα peptide bound to I-A). Proliferation was measured by $^3$H-thymidine incorporation for the last 24 h of a 48 h culture. TIRAP peptide-treated DCs from either wild-type or MyD88-deficient mice were unable to induce T cell proliferation (FIG. 6C). These data demonstrate that TIRAP can activate a pathway that induces DC maturation and suggest that TIRAP is responsible for the LPS-induced maturation in MyD88-deficient DCs. As these results indicate, TIRAP appears to be critical for the ability of DCs to produce cytokines, upregulate costimulatory molecules, and prime naive T cells in response to LPS stimulation.

Example 6

Generation of TIRAP Knock-Out Mice

To make the targeting construct, 7.4 kb of the mouse TIRAP gene was cloned by RT-PCR and sublconed into a pEasy Flox vector. The second exon of the mouse TIRAP gene, which encodes 610 bp of the 730 bp-coding sequence, was then replaced with neomycin in the pEasy Flox vector using techniques standard in the art. It is our current understamiding that the 3.7 kb of the 5' flanking sequences and 3.1 kb of the 3' flanking sequences direct homologous recombination at the mouse TIRAP locus.

Embryonic stem cells were then transfected with the targeting construct by electroporation, and selected using G418 and gangcyclovir. To identify clones that have integrated the targeting construct by homologous recombination, clones were screened by Southern analysis. Two positive clones were then chosen for injection into pseudopregnant mothers.

From these injected clones developed two highly chimeric male mice, which were bred with female littermates. Tail DNAs were then obtained from pups for Southern analysis. Germline transmission was obtained with two mice. Lastly, these two F1 mice were interbred to generate homozygous TIRAP knockout mice, which were born at the expected Mendelian frequency.

Example 7

Exposure of Cells of TIRAP Knock-Out Mice to TLR Ligands

Figure 8:
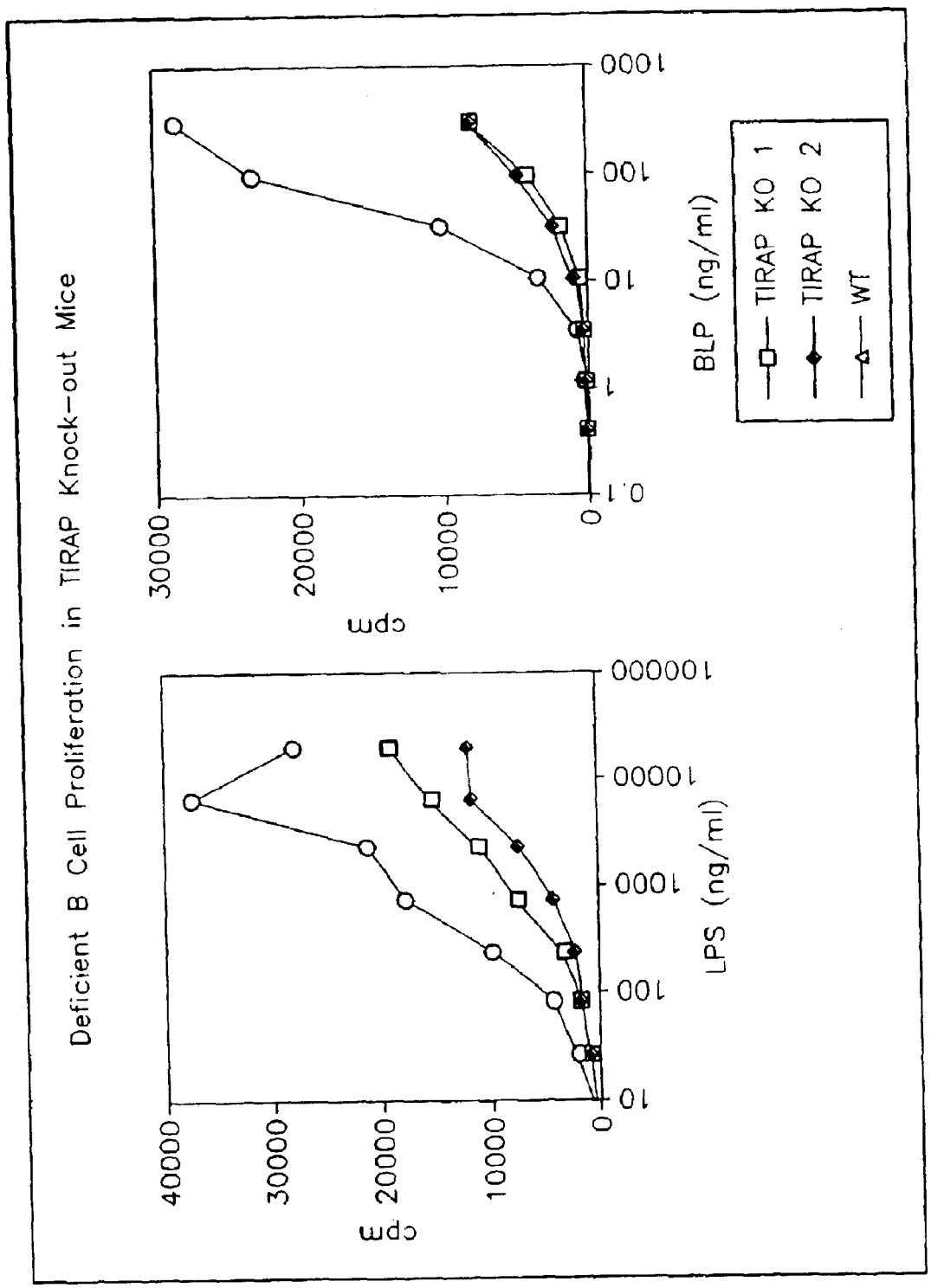
FIG. 8 graphically represents deficient B cell proliferation in cells from TIRAP knock-out mice which were exposed to 3H thymidine. The open square and black diamond denote the results from TIRAP knock-out mice K01 and K02, respectively, and the open triangle represents a wild-type (WT) control. As a measure of B cell proliferation, a beta radiation counter determined the amount 3H thymidine incorporated into B cells by counting the number of radioactive emissions over time.

FIG. 8 graphically represents deficient B cell proliferation in cells from the TIRAP knock-out mice produced in the manner described in Example 6. Splenocytes were taken from wild-type and the TIRAP knock-out mice, counted and plated into 96 well plates at about 100,000 cells/100 ml. Serial dilutions of LPS (starting from 20 ug./ml. final concentration) and BLP (starting from 300 ng./ml. final concentration) were added to the splenocytes. Thirty-six hours later, radioactive 3H thymidine was added to each well. The incorporation of 3H thymidine into proliferating B cells was assessed 12 hours later by use of a beta counter. As the results shown FIG. 8 indicate, the amount of 3H thymidine incorporated into the cells, and thus the B cells' proliferation, was significantly reduced in the TIRAP knock-out mice splenocytes as compared to the wild-type mouse splenocytes.

Figure 9:
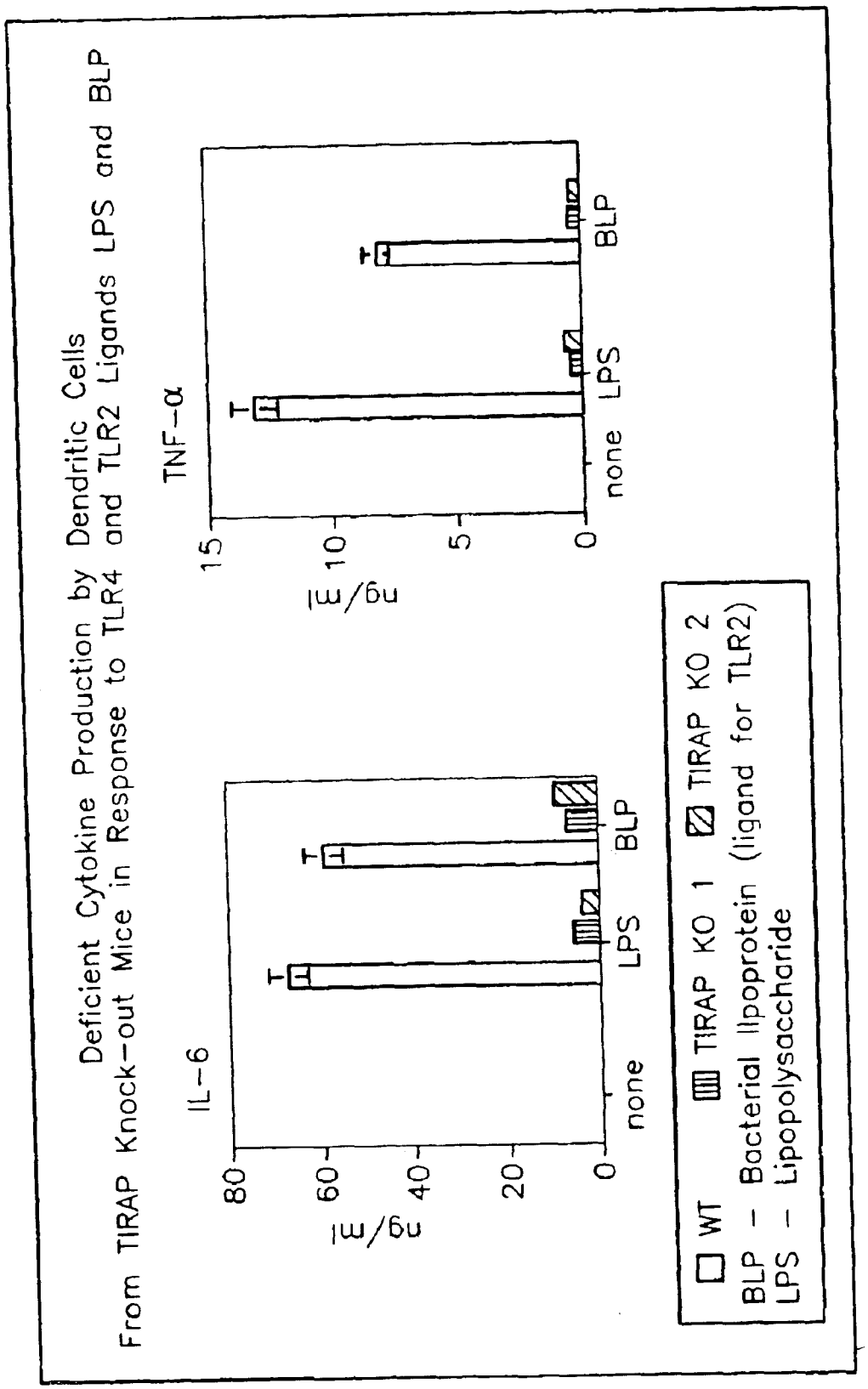
FIG. 9 graphically represents deficient cytokine production by dendritic cells from TIRAP knock-out mice. The black and striped bars denote the results from TIRAP knock-out mice K01 and K02, respectively, and the open bar represents a wild-type (WT) control. As a measure of cytokine production, B cells were stimulated with LPS and BLP and harvested for ELISA, using IL-6 and TNF-α capture antibodies and appropriate biotin-conjugated detection antibodies.

FIG. 9 graphically represents cytokine production by dendritic cells from TIRAP knock-out mice produced in the manner described in Example 6. Bone marrow-derived cells were taken from the wild-type and TIRAP knock-out mice, and were cultured for five days in complete RPMI supplemented with GM-CSF in 24-well plates. On day 5, the cells were counted and replated into 24-well plates at about 100,000 cells/ml., and stimulated overnight with LPS (10 ng./ml.) or BLP (100 ng./ml.). Twenty-four hours post stimulation, supernatants were harvested for ELISA.

For the ELISA analysis, plates were coated with appropriate capture antibodies, namely IL-6 or TNF-α, washed, and then coated with supernatants from the various samples. After overnight incubation, the supernatant was washed off, and the appropriate biotin-conjugated detection antibody was added. Streptavidin-HRP was then added, followed by its substrate. Colorimetric changes were monitored using an ELISA plate reader. Quantification of cytokine concentrations in supernatants was done by comparison with a standard made using the respective recombinant cytokines. As the results shown FIG. 9 indicate, the amount of cytokine production by dendritic cells was significantly reduced in the TIRAP knock-out mice dendritic cells as compared to the wild-type mouse dendritic cells.

What is claimed is:

1. An isolated polypeptide having at least 92% identity to SEQ ID NO:11.

2. A fusion protein comprising the isolated polypeptide of claim 1.

3. A drug screening method comprising the steps of:
   a. providing a polypeptide comprising at least the TIRAP-binding domain of TLR4;
   b. providing a TIRAP inhibitor polypeptide;
   c. providing a candidate compound;
   d. contacting the candidate compound with the polypeptide comprising the TIRAP-binding domain of TLR4 and the TIRAP inhibitor polypeptide; and
   e. determining whether the candidate compound competes with the binding of either of the polypeptide comprising the TIRAP-binding domain of TLR4 or the TIRAP inhibitor polypeptide, wherein the TIRAP-binding domain of TLR4 comprises TLR4 and the TIRAP inhibitor polypeptide consists of a TIRAP inhibitor polypeptide having at least 92% identity to SEQ ID NO:11.

4. The isolated polypeptide of claim 1, wherein the polypeptide is SEQ ID NO:11.

5. The isolated polypeptide of claim 1, wherein the polypeptide is SEQ ID NO:11, but for His substituted for Pro at amino acid position 24.

6. A fusion protein comprising the isolated polypeptide of claim 4.

7. A fusion protein comprising the isolated polypeptide of claim 5.

8. The drug screening method of claim 3, wherein the TIRAP inhibitor polypeptide is SEQ ID NO: 11.

9. The drug screening method of claim 3, wherein the TIRAP inhibitor polypeptide is SEQ ID NO: 11 but for the substitution of His for Pro at amino acid position 24.

* * * * *

UNITED STATES PATENT AND TRADEMARK OFFICE
CERTIFICATE OF CORRECTION

PATENT NO. : 6,960,343 B2 Page 1 of 1
APPLICATION NO. : 10/188947
DATED : November 1, 2005
INVENTOR(S) : Ruslan Medzhitov, Tiffany Horng and Gregory Barton It is certified that error appears in the above-identified patent and that said Letters Patent is hereby corrected as shown below:

Column 38,
Line 1, delete "a" and insert -- the polypeptide of the --.

Signed and Sealed this

Twenty-seventh Day of June, 2006

JON W. DUDAS
*Director of the United States Patent and Trademark Office*

UNITED STATES PATENT AND TRADEMARK OFFICE
CERTIFICATE OF CORRECTION

PATENT NO. : 6,960,343 B2 Page 1 of 1
APPLICATION NO. : 10/188947
DATED : November 1, 2005
INVENTOR(S) : Ruslan Medzhitov, Tiffany Horng and Gregory Barton It is certified that error appears in the above-identified patent and that said Letters Patent is hereby corrected as shown below:

In Column 1, delete lines 18-20 that state the following:

"This application was funded, at least in part, by a grant from the
United States Government, which may have certain rights therein."

and replace with the following:

-- The invention was supported, in whole or in part, by a
government grant, AI44220, from the National Institutes
of Health. The Government has certain rights in this invention. --

Signed and Sealed this

First Day of April, 2008

JON W. DUDAS
*Director of the United States Patent and Trademark Office*

SEQUENCE LISTING

<160> NUMBER OF SEQ ID NOS: 12

<210> SEQ ID NO 1
<211> LENGTH: 708
<212> TYPE: DNA
<213> ORGANISM: Homo sapiens
<220> FEATURE:
<221> NAME/KEY: misc_feature
<223> OTHER INFORMATION: TIRAP polynucleotide

<400> SEQUENCE: 1

| | | | | | |
|---|---|---|---|---|---|
| atggcatcat | cgacctccct | cccagctcct | ggctctcggc | ctaagaagcc | tctaggcaag | 60 |
| atggctgact | ggttcaggca | gaccctgctg | aagaagccca | agaagaggcc | caactcccca | 120 |
| gaaagcacct | ccagcgatgc | ttcacagcct | acctcacagg | acagcccact | accccaagc | 180 |
| ctcagctcag | tcacgtctcc | cagcctgcca | cccacacatg | cgagtgacag | tggcagtagt | 240 |
| cgctggagca | aagactatga | cgtctgcgtg | tgccacagtg | aggaagacct | ggtggccgcc | 300 |
| caggacctgg | tctcctactt | ggaaggcagc | actgccagcc | tgcgctgctt | cctgcaactc | 360 |
| cgggatgcaa | ccccaggcgg | cgctatagtg | tccgagctgt | gccaggcact | gagcagtagt | 420 |
| cactgccggg | tgctgctcat | cacgccgggc | ttccttcagg | accctggtg | caagtaccag | 480 |
| atgctgcagg | ccctgaccga | ggctccaggg | ccgagggct | gcaccatccc | cctgctgtcg | 540 |
| ggcctcagca | gagctgccta | cccacctgag | ctccgattca | tgtactacgt | cgatggcagg | 600 |
| ggccctgatg | gtggctttcg | tcaagtcaaa | gaagctgtca | tgcgttgtaa | gctactacag | 660 |
| gagggagaag | gggaacggga | ttcagctaca | gtatctgatc | tactttga | | 708 |

<210> SEQ ID NO 2
<211> LENGTH: 726
<212> TYPE: DNA
<213> ORGANISM: Mus sp.
<220> FEATURE:
<221> NAME/KEY: misc_feature
<223> OTHER INFORMATION: TIRAP polynucleotide
<221> NAME/KEY: misc_feature
<222> LOCATION: (417)..(417)
<223> OTHER INFORMATION: n=A,C,T,G

<400> SEQUENCE: 2

| | | | | | |
|---|---|---|---|---|---|
| atggcttcat | cctcctccgt | cccagcctcc | tccactccgt | ccaagaagcc | tcgagacaag | 60 |
| atagctgact | ggttcaggca | ggctctgttg | aagaagccca | agaagatgcc | gatctcccag | 120 |
| gaaagccacc | tctatgatgg | ttcacagaca | gccacacagg | atggtctctc | accctcgagc | 180 |
| tgcagctcac | ccccgagtca | cagttcaccc | gagagccgta | gctcaccctc | gagctgcagt | 240 |
| tcaggaatgt | cacctacctc | gccaccaaca | cacgtggaca | gcagcagcag | cagcagtggc | 300 |
| cgctggagca | aagactacga | tgtctgcgtg | tgccacagtg | aggaggactt | ggaggcggcc | 360 |
| caggagctgg | tctcctactt | ggagggtagc | caggccagtc | tacgctgctt | cctgcanctt | 420 |
| cgggatgcag | ccccggtgg | cgccattgtt | tcggagctat | gccaggcact | gagtcgtagt | 480 |
| cactgccgtg | tgctgctcat | cactccaggc | ttccttcggg | accctggtg | caagtaccag | 540 |
| atgctgcagg | ccctgacgga | ggccccggcg | tcgagggtt | gcaccatacc | cctgctgtcc | 600 |
| ggcctgtcca | gagccgccta | cccgccggaa | ctccgattca | tgtactatgt | ggatggcaga | 660 |
| ggcaaggacg | gaggcttta | ccaagtcaag | gaggctgtta | tacactatct | ggagacacta | 720 |
| agctga | | | | | | 726 |

<210> SEQ ID NO 3
<211> LENGTH: 235
<212> TYPE: PRT
<213> ORGANISM: Homo sapiens
<220> FEATURE:
<221> NAME/KEY: MISC_FEATURE
<223> OTHER INFORMATION: TIRAP polypeptide -continued

<400> SEQUENCE: 3

```
Met Ala Ser Ser Thr Ser Leu Pro Ala Pro Gly Ser Arg Pro Lys Lys
1               5                   10                  15

Pro Leu Gly Lys Met Ala Asp Trp Phe Arg Gln Thr Leu Leu Lys Lys
            20                  25                  30

Pro Lys Lys Arg Pro Asn Ser Pro Glu Ser Thr Ser Ser Asp Ala Ser
        35                  40                  45

Gln Pro Thr Ser Gln Asp Ser Pro Leu Pro Pro Ser Leu Ser Ser Val
    50                  55                  60

Thr Ser Pro Ser Leu Pro Pro Thr His Ala Ser Asp Ser Gly Ser Ser
65                  70                  75                  80

Arg Trp Ser Lys Asp Tyr Asp Val Cys Val Cys His Ser Glu Glu Asp
                85                  90                  95

Leu Val Ala Ala Gln Asp Leu Val Ser Tyr Leu Glu Gly Ser Thr Ala
            100                 105                 110

Ser Leu Arg Cys Phe Leu Gln Leu Arg Asp Ala Thr Pro Gly Gly Ala
        115                 120                 125

Ile Val Ser Glu Leu Cys Gln Ala Leu Ser Ser His Cys Arg Val
    130                 135                 140

Leu Leu Ile Thr Pro Gly Phe Leu Gln Asp Pro Trp Cys Lys Tyr Gln
145                 150                 155                 160

Met Leu Gln Ala Leu Thr Glu Ala Pro Gly Ala Glu Gly Cys Thr Ile
                165                 170                 175

Pro Leu Leu Ser Gly Leu Ser Arg Ala Ala Tyr Pro Pro Glu Leu Arg
            180                 185                 190

Phe Met Tyr Tyr Val Asp Gly Arg Gly Pro Asp Gly Gly Phe Arg Gln
        195                 200                 205

Val Lys Glu Ala Val Met Arg Cys Lys Leu Leu Gln Glu Gly Glu Gly
    210                 215                 220

Glu Arg Asp Ser Ala Thr Val Ser Asp Leu Leu
225                 230                 235
```

<210> SEQ ID NO 4
<211> LENGTH: 241
<212> TYPE: PRT
<213> ORGANISM: Mus sp.
<220> FEATURE:
<221> NAME/KEY: MISC_FEATURE
<223> OTHER INFORMATION: TIRAP polypeptide

<400> SEQUENCE: 4

```
Met Ala Ser Ser Ser Val Pro Ala Ser Ser Thr Pro Ser Lys Lys
1               5                   10                  15

Pro Arg Asp Lys Ile Ala Asp Trp Phe Arg Gln Ala Leu Leu Lys Lys
            20                  25                  30

Pro Lys Lys Met Pro Ile Ser Gln Glu Ser His Leu Tyr Asp Gly Ser
        35                  40                  45

Gln Thr Ala Thr Gln Asp Gly Leu Ser Pro Ser Cys Ser Ser Pro
    50                  55                  60

Pro Ser His Ser Ser Pro Glu Ser Arg Ser Pro Ser Ser Cys Ser
65                  70                  75                  80

Ser Gly Met Ser Pro Thr Ser Pro Pro Thr His Val Asp Ser Ser Ser
                85                  90                  95
```

```
Ser Ser Ser Gly Arg Trp Ser Lys Asp Tyr Asp Val Cys Val Cys His
            100                 105                 110
Ser Glu Glu Asp Leu Glu Ala Ala Gln Glu Leu Val Ser Tyr Leu Glu
        115                 120                 125
Gly Ser Gln Ala Ser Leu Arg Cys Phe Leu Gln Leu Arg Asp Ala Ala
    130                 135                 140
Pro Gly Gly Ala Ile Val Ser Glu Leu Cys Gln Ala Leu Ser Arg Ser
145                 150                 155                 160
His Cys Arg Val Leu Leu Ile Thr Pro Gly Phe Leu Arg Asp Pro Trp
                165                 170                 175
Cys Lys Tyr Gln Met Leu Gln Ala Leu Thr Glu Ala Pro Ala Ser Glu
            180                 185                 190
Gly Cys Thr Ile Pro Leu Leu Ser Gly Leu Ser Arg Ala Ala Tyr Pro
        195                 200                 205
Pro Glu Leu Arg Phe Met Tyr Tyr Val Asp Gly Arg Gly Lys Asp Gly
    210                 215                 220
Gly Phe Tyr Gln Val Lys Glu Ala Val Ile His Tyr Leu Glu Thr Leu
225                 230                 235                 240
Ser

<210> SEQ ID NO 5
<211> LENGTH: 39
<212> TYPE: DNA
<213> ORGANISM: Homo sapiens
<220> FEATURE:
<221> NAME/KEY: misc_feature
<223> OTHER INFORMATION: naturally occurring TIRAP inhibitory peptide

<400> SEQUENCE: 5
ctgcaactcc gggatgcaac cccaggcggc gctatagtg                      39

<210> SEQ ID NO 6
<211> LENGTH: 42
<212> TYPE: DNA
<213> ORGANISM: Homo sapiens
<220> FEATURE:
<221> NAME/KEY: misc_feature
<223> OTHER INFORMATION: degenerate TIRAP polynucleotide
<221> NAME/KEY: misc_feature
<222> LOCATION: (1)..(42)
<223> OTHER INFORMATION: Y=C,T; N=A,G,C,T; R=A,G; H=A,C,T; W=A,T; S=G,C

<400> SEQUENCE: 6
ytncarytnm gngaygcnac nccnggnggn gcnathgtnw sn                   42

<210> SEQ ID NO 7
<211> LENGTH: 42
<212> TYPE: DNA
<213> ORGANISM: Mus sp.
<220> FEATURE:
<221> NAME/KEY: misc_feature
<223> OTHER INFORMATION: naturally occurring TIRAP inhibitory peptide

<400> SEQUENCE: 7
ctgcagcttc gggatgcagc cccgggtggc gccattgttt cg                   42

<210> SEQ ID NO 8
<211> LENGTH: 42
<212> TYPE: DNA
<213> ORGANISM: Mus sp.
```

```
<220> FEATURE:
<221> NAME/KEY: misc_feature
<223> OTHER INFORMATION: degenerate TIRAP polynucleotide
<221> NAME/KEY: misc_feature
<222> LOCATION: (1)..(42)
<223> OTHER INFORMATION: Y=C,T; N=A,G,C,T; R=A,G; M=A,C; H=A,C,T;
      W=A,T; S=G,C

<400> SEQUENCE: 8
ytncarytnm gngaygcngc nccngggnggn gcnathgtnw sn                    42

<210> SEQ ID NO 9
<211> LENGTH: 14
<212> TYPE: PRT
<213> ORGANISM: Homo sapiens
<220> FEATURE:
<221> NAME/KEY: MISC_FEATURE
<223> OTHER INFORMATION: TIRAP inhibitory polypeptide

<400> SEQUENCE: 9

Leu Gln Leu Arg Asp Ala Thr Pro Gly Gly Ala Ile Val Ser
1               5                   10

<210> SEQ ID NO 10<211>   14<212>   PRT<213>   Mus sp.<220><221>
      MISC_FEATURE<223>   TIRAP inhibitory polypeptide
<211> LENGTH:
<212> TYPE:
<213> ORGANISM:

<400> SEQUENCE: 10

Leu Gln Leu Arg Asp Ala Ala Pro Gly Gly Ala Ile Val Ser
1               5                   10

<210> SEQ ID NO 11
<211> LENGTH: 30
<212> TYPE: PRT
<213> ORGANISM: Artificial Sequence
<220> FEATURE:
<223> OTHER INFORMATION: TIRAP/Antennapedia fusion protein
<221> NAME/KEY: MISC_FEATURE
<223> OTHER INFORMATION: TIRAP/Antennapedia fusion protein

<400> SEQUENCE: 11

Arg Gln Ile Lys Ile Trp Phe Gln Asn Arg Arg Met Lys Trp Lys Lys
1               5                   10                  15

Leu Gln Leu Arg Asp Ala Ala Pro Gly Gly Ala Ile Val Ser
            20                  25                  30

<210> SEQ ID NO 12
<211> LENGTH: 14
<212> TYPE: PRT
<213> ORGANISM: Artificial Sequence
<220> FEATURE:
<223> OTHER INFORMATION: TIRAP inhibitory peptide
<221> NAME/KEY: MISC_FEATURE
<223> OTHER INFORMATION: TIRAP inhibitory polypeptide

<400> SEQUENCE: 12

Val Ser Asp Arg Asp Val Leu Pro Gly Thr Cys Val Trp Ser
1               5                   10
```